(12) United States Patent
Falder et al.

(10) Patent No.: US 7,674,473 B2
(45) Date of Patent: Mar. 9, 2010

(54) ANTI-MICROBIAL COMPOSITION

(75) Inventors: Stephen Brian Falder, Knutsford (GB); David Rawden, Stockport (GB)

(73) Assignee: Byotrol PLC (GB)

( * ) Notice: Subject to any disclaimer, the term of this patent is extended or adjusted under 35 U.S.C. 154(b) by 22 days.

(21) Appl. No.: 10/039,677

(22) Filed: Jan. 4, 2002

(65) Prior Publication Data

US 2003/0031687 A1     Feb. 13, 2003

Related U.S. Application Data

(63) Continuation-in-part of application No. 09/756,457, filed on Jan. 8, 2001, now abandoned.

(30) Foreign Application Priority Data

Jan. 4, 2001    (GB)   ............... 0100155.1

(51) Int. Cl.
     *A01N 25/00*     (2006.01)
(52) U.S. Cl. .................................... 424/405
(58) Field of Classification Search ............ 424/404, 424/405, 400

See application file for complete search history.

(56) References Cited

U.S. PATENT DOCUMENTS

| | | | |
|---|---|---|---|
| 3,970,755 A | 7/1976 | Gazzard et al. | 424/270 |
| 4,173,643 A | 11/1979 | Law | 424/270 |
| 4,698,148 A | 10/1987 | Keane | 208/390 |
| 4,718,941 A | 1/1988 | Halverson et al. | 75/236 |
| 4,788,176 A | 11/1988 | Wieserman et al. | 502/401 |
| 4,902,349 A | 2/1990 | Wakizaka et al. | 106/277 |
| 5,178,495 A | 1/1993 | Cameron | 405/303 |
| 5,244,666 A | 9/1993 | Murley | 424/405 |
| 5,529,690 A | 6/1996 | Pashley et al. | 210/490 |
| 5,538,667 A | 7/1996 | Hill et al. | 252/312 |
| 5,645,841 A | 7/1997 | Hill et al. | 424/401 |
| 5,651,959 A | 7/1997 | Hill et al. | 424/49 |
| 5,665,374 A | 9/1997 | Hill et al. | 424/435 |
| 5,670,055 A | 9/1997 | Yu et al. | 210/698 |
| 5,681,637 A | 10/1997 | Kessler et al. | 428/85 |
| 5,688,449 A | 11/1997 | Fox | 264/54 |
| 5,711,936 A | 1/1998 | Hill et al. | 424/49 |
| 5,730,967 A | 3/1998 | Hill et al. | 424/78.01 |
| 5,733,529 A | 3/1998 | Hill et al. | 424/49 |
| 5,733,536 A | 3/1998 | Hill et al. | 424/70.12 |
| 5,834,114 A | 11/1998 | Economy et al. | 428/368 |
| 5,856,245 A | 1/1999 | Caldwell et al. | 442/76 |
| 5,869,172 A | 2/1999 | Caldwell | 428/306.6 |
| 5,874,164 A | 2/1999 | Caldwell | 428/306.6 |
| 5,955,093 A | 9/1999 | Woo et al. | 424/401 |
| 6,039,965 A | 3/2000 | Dolan et al. | 424/405 |
| 6,107,268 A | 8/2000 | Yahiaoui et al. | 510/438 |
| 6,656,923 B1 * | 12/2003 | Trinh et al. | 514/58 |

FOREIGN PATENT DOCUMENTS

| | | | |
|---|---|---|---|
| CA | 1087955 | * | 10/1980 |
| EP | 0181182 A2 | | 5/1986 |
| EP | 0206028 A1 | | 12/1986 |
| EP | 0233954 A2 | | 9/1987 |
| EP | 0340938 | | 11/1989 |
| EP | 0513637 | | 11/1992 |
| GB | 2247171 | * | 2/1992 |
| WO | WO 91/07090 | | 5/1991 |
| WO | WO 92/21320 | | 12/1992 |
| WO | WO 93/10209 | | 5/1993 |
| WO | WO 96/39249 | | 12/1996 |
| WO | WO 98/35933 | | 8/1998 |
| WO | WO 00/00024 | | 1/2000 |
| WO | WO - 0000024 | * | 1/2000 |
| WO | WO 01/64034 | | 9/2001 |

OTHER PUBLICATIONS

Abstract of Japanese Patent JP4065409A2 titled Surface-Modifying Agent for Polymeric Material Curable with Actinic Energy Ray and Production Thereof issued Mar. 2, 1992.

Abstract of Japanese Patent JP4110329A2 titled Surface Modifier for Active Energy Ray-Curable Polymer Material and Preparation Thereof issued Apr. 10, 1992.

Abstract of Japanese Patent JP57179522A2 titled Deodorizing Filter for Air Conditioner issued Nov. 5, 1982.

Abstract of Japanese Patent JP7252177A2 titled Surface Modifier and Method for Surface Modification Using the Same issued Oct. 3, 1995.

Abstract of Japanese Patent JP7292289A2 titled Antibacterial Floor Coating Material and Coated Floor Surface issued Nov. 7, 1995.

Abstract of Japanese Patent JP9256217A2 titled Polytetrafluoroethylene Fiber and Its Production issued Sep. 30, 1997.

Abstract of Japanese Patent JP10016158A2 titled Antibacterial Biaxially Oriented Polypropylene Film issued Jan. 20, 1998.

Abstract of Japanese Patent JP10095468A2 titled Container Made of Antibacterial Material issued Apr. 14, 1998.

Abstract of Japanese Patent JP10095469A2 titled Storage Container for Medical Instrument and Medical Material issued Apr. 14, 1998.

(Continued)

*Primary Examiner*—Alton N Pryor
(74) *Attorney, Agent, or Firm*—Nelson Mullins Riley & Scarborough LLP

(57) ABSTRACT

An anti-microbial composition comprising (i) a first compound having a high surface tension of from 20 to 35 mN/m, (ii) a second compound having a low surface tension of from 8 to 14 mN/m, (iii) a first anti-microbial agent and (iv) a polar solvent, wherein the composition acts substantially to prevent the formation of microbial colonies on or at a surface of the composition.

53 Claims, 4 Drawing Sheets

OTHER PUBLICATIONS

Abstract of Japanese Patent JP10095935A2 titled Antimicrobial Interior Material issued Apr. 14, 1998.

Abstract of Japanese Patent JP10152396A2 titled Material Having Crystalline Oriented Membrane of Titanium Dioxide and Its Production issued Jun. 9, 1998.

Article published in PNAS May 22, 2001, vol. 98, No. 11, pp. 5981-5985 by Joerg C. Tiller, et al., entitled Designing Surfaces That Kill Bacteria on Contact.

Abstract of Japanese Patent JP9175904 titled Improved Water-Based Suspended Agrochemical Composition published Aug. 7, 1997.

* cited by examiner

ANTI-MICROBIAL COMPOSITION

This application is a continuation-in-part of application Ser. No. 09/756,457 filed on Jan. 8, 2001 now abandoned. This application claims priority under 35 U.S.C. §119 to Great Britain Application No. 0100155.1 filed on Jan. 4, 2001. Both applications are incorporated herein in their entireties by reference thereto.

This invention relates to anti-microbial compositions and to formulations including the anti-microbial compositions.

BACKGROUND, SUMMARY AND DETAILED DESCRIPTION OF THE INVENTION

Figure 1:
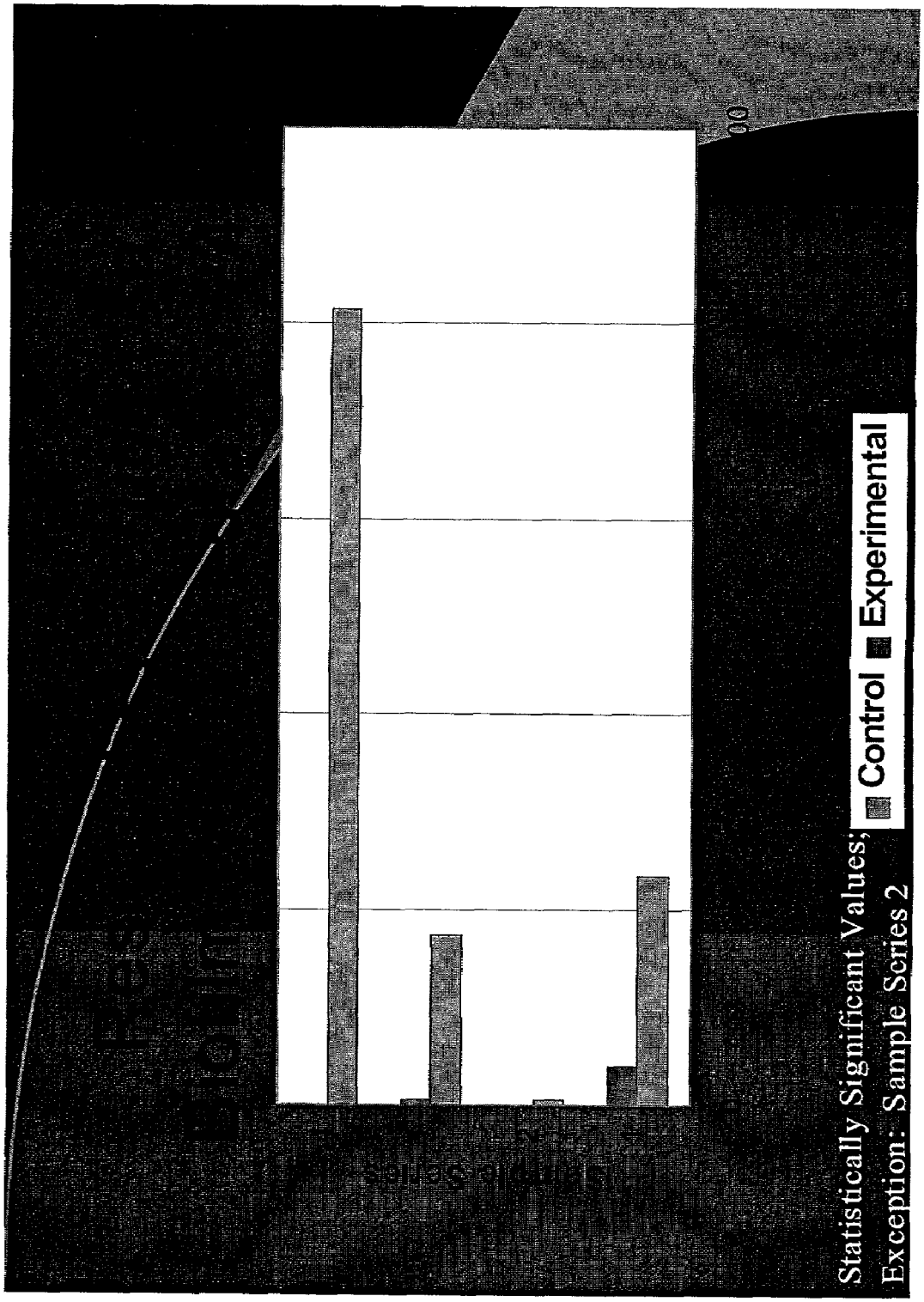
FIG. 1 illustrates the residual *P. aeruginosa* biofilm recovered after 24 hours for the experimental and control samples.

Microorganisms can be found in many environments and are known to present health hazards due to infection or contamination.

When microorganisms are present on the surface of a substrate they can replicate rapidly to form colonies. Virtually all microorganisms replicate in this way. The microbial colonies form a coating, which is known as a biofilm, on the substrate surface. Biofilms are more hazardous to health than individual microorganisms. Some microorganisms also produce polysaccharide coatings, which makes them more difficult to destroy.

A biofilm can be formed by a single bacterial species but more often biofilms consist of several species of bacteria, as well as fungi, algae, protozoa, debris and corrosion products. Essentially, biofilm may form on any surface exposed to bacteria and some amount of water, which is needed to allow metabolic processes.

Biofilm formation occurs via three distinct stages. The three stages are (i) adhesion or attachment, (ii) proliferation and (iii) biofilm differentiation.

Before stage (i) can occur, the microorganisms must be transported to a surface. This occurs by random contact with the surface due to Brownian motion, sedimentation, active transport or chemotaxis. Once the microorganisms have been transported to a surface, initial adhesion to the surface occurs, for example, as a result of Lifshitz-van der Waals forces, acid-base interactions and electrostatic forces between negatively charged microorganisms and positively charged domains.

The microorganisms then excrete extracellular polymers, which form an extracellular polymeric substance composed of polysaccharides, nucleic acids, amphiphilic, humic substances and proteins. The extracellular polymeric substance forms a matrix that interconnects and binds together microorganisms attached to the surrounding surface. Thus, the microorganisms are anchored to the surface, which can be all kinds of materials such as metals, plastics, soil particles, medical implant materials and tissue.

Once anchored to a surface, biofilm microorganisms carry out a variety of detrimental or beneficial reactions (by human standards), depending on the surrounding environmental conditions. It is, therefore, desirable to remove and/or destroy the biofilm microorganisms on the surface.

The pasteurisation process has been used for a number of years to destroy microorganisms. In this process, the microorganisms are subjected to high temperature and, optionally, high pressure.

Microorganisms can also be removed from surfaces by simple washing and sanitisation of the surface with fresh water or with soap or simple detergents. Washing removes the majority of the microorganisms but does not prevent the growth of any microorganisms that remain.

Microorganisms can also be destroyed by contacting them with anti-microbial agents, which are poisonous to microorganisms. A large number of anti-microbial agents are known. For example, bacteriocidal, fungicidal, algicidal, yeasticidal and moldicidal agents are known. The anti-microbial agents can destroy microorganisms that are present in a wide range of environments such as medical, industrial, commercial, domestic and marine environments. Many of the known anti-microbial agents have previously been included in compositions for use in various applications and environments.

For example, EP-A-0233954 describes a composition for treating a solid material to give it anti-microbial, hydrophilic and anti-static properties. The composition comprises a quaternary ammonium salt-containing silane, an organopolysiloxane and, optionally, an organic solvent.

EP-A-0206028 describes a method of promoting the growth of plants. The method comprises applying a specific quaternary ammonium compound, which may be formulated as an aqueous solution.

EP-A-0181182 describes an emulsion that comprises water, a water immiscible liquid, a cationic silane and, optionally, a co-surfactant.

WO-A-93/10209 describes a composition for sterilising, disinfecting, cleaning and lubricating medical and dental devices. The composition comprises a water-soluble or water-dispersible disinfecting and/or sterilising agent, a surfactant and a water-soluble polymer having lubricating characteristics.

WO-A-92/21320 describes medicated shampoo compositions that include anti-microbial agents. The compositions include an anti-microbial agent comprising a fatty acid monoester of a polyhydroxyl alcohol, a chelating agent and a cleansing agent.

U.S. Pat. No. 5,244,666 describes a liquid preparation for use as a presurgical skin scrub or wound disinfectant. The preparation comprises a quaternary ammonium compound, a substituted phenolic compound, water and sodium lauryl sulfate.

JP-9175904 describes an agricultural composition that comprises 1,2-benzisothiazoline-3-on, dimethyl polysiloxane, water and N-t-butyl-N'-(4-ethylbenzoyl)-3,5-dimethylbenzohydrazide.

The known anti-microbial agents and the compositions that contain these anti-microbial agents destroy microorganisms by a number of different mechanisms.

Chlorinated compounds, such as hypochlorites (bleaches) can act as anti-microbial agents. Traditional bleach includes sodium hypochlorite. Sodium hypochlorite breaks down to provide chloride and chlorate. Chlorate is highly toxic to life forms.

Although bleaches are useful for destroying a wide range of microorganisms, typically they only work for a short term. This is because their efficacy decreases rapidly once they have broken down. Thus, bleaches do not provide long-term passive anti-microbial control and sanitisation. By "passive control" we mean that the substrate counters microbial infection on its own by some property within it, so that it does not require a cleaning regime to be effective at controlling microorganisms. Furthermore, bleaches can decompose to produce chlorine gas, which is known to be harmful to the environment. Thus, the use of chlorine-containing compounds is to be avoided where possible.

Other known anti-microbial agents include phenol and compounds thereof, arsenene and salts of arsenic. Examples of useful phenol compounds include polychlorinated biphenols, such as triclosan. Other known anti-microbial agents that are commonly used include organic and inorganic salts of heavy metals such as silver, copper or tin. For example, colloidal silver can be used.

Phenol compounds typically are highly toxic to humans and animals as well as to microorganisms. Consequently the anti-microbial agents are dangerous to handle, and specialist handling, treatment and equipment are therefore required in order to handle these anti-microbial agents safely. Anti-microbial agents can also be difficult to handle if they are strongly acidic or alkaline. The manufacture and disposal of compositions comprising this type of anti-microbial agent can, therefore, be problematic. There can also be problems associated with the use of compositions containing highly toxic anti-microbial agents, particularly in consumer materials where it is difficult to ensure that they are used for designated purposes.

Herein, unless the context indicates otherwise, "toxicity" is intended to refer to toxicity to complex organisms such as mammals. References to "toxic" are to be construed accordingly.

Anti-microbial agents based on phenols and heavy metals typically are only effective against certain microorganisms, such as fungi. Their use is, therefore, limited because they are not effective against all types of microorganism. Additionally, some anti-microbial agents, such as biphenol, do not remain active for extended periods because they are volatile and do not remain on the surface to which they are applied.

Once the anti-microbial agents and/or their breakdown products enter the environment then they can affect the health of life forms that they were not intended to affect. Moreover, the anti-microbial agents and their breakdown products are often highly stable and can cause environmental problems for long periods of time. For example, the metal salts produce toxic rinsates, which are poisonous to aquatic life. Once the toxic compounds enter the environment they are not easily broken down and can cause persistent problems or unknown consequences. For example, colloidal silver, tributyl tin and diuron can remain in the environment for extended periods of time. The combustion of polychlorinated biphenol compounds produces dioxins, which are harmful to the environment.

Other anti-microbial agents currently in use include antibiotic type compounds, such as penicillin. Antibiotics disrupt the biochemistry within microorganisms, for example by selectively diluting solutions to destroy or inhibit the growth of harmful microorganisms.

Although antibiotics are effective, it is currently believed that they may selectively permit the development of resistant strains of the species that they are used against. These resistant strains are then able to reproduce unimpeded by the use of known antibiotics. Thus, there is a growing concern that wide and uncontrolled use of antibiotic materials in the wider environment, as opposed to their controlled use in medical contexts, could produce significant long-term risks. Antibiotics are, therefore, considered inappropriate for general use in a non-medical environment.

There is also a risk that resistant strains can occur with other types of anti-microbial agent, which can have a biochemical effect. For example, triclosan resistance is discussed in Chuanchuen et al., "Multidrug Efflux Pumps and Triclosan Resistance in *Pseudomonas Aeruginosa*", 100$^{th}$ General Meeting of the American Society for Microbiology, May 21-25, LA; Meade et al., "Unique Mechanism of Triclosan Resistance Identified in Environmental Isolates", 100$^{th}$ General Meeting of the American Society for Microbiology, May 21-25, LA; Suzangar et al., "An Evaluation of Biocide-containing Materials for their Surface Colonisation-resistance and Other Properties", 100$^{th}$ General Meeting of the American Society for Microbiology, May 21-25, LA.

Thus, there is a need for an anti-microbial composition that is effective against a wide variety of microorganisms for long periods of time and which can be used safely and conveniently.

According to an aspect of the invention there is provided an anti-microbial composition comprising (i) a first compound having a high surface tension of from 20 to 35 mN/m, (ii) a second compound having a low surface tension of from 8 to 14 mN/m, (iii) a first anti-microbial agent and (iv) a polar solvent, wherein the composition acts substantially to prevent the formation of microbial colonies on or at a surface of the composition.

The anti-microbial composition of the invention is highly effective and works with a broad range of microorganisms.

It seems that the anti-microbial composition of the invention works by providing a surface to which microorganisms are substantially prevented from adhering and attaching. In other words, the composition of the invention substantially prevents the occurrence of stage (i) of the biofilm formation process. This means that the microorganisms cannot then multiply and form biofilms.

It is thought that the surface provided by the anti-microbial composition prevents adhesion and attachment of microorganisms due to the interaction of two compounds of high and low surface tension, which have opposing surface tension effects.

The prevention of the formation of a biofilm and the greatly reduced and attenuated colonies of microorganisms provides a substantially reduced risk due to infection or contamination. This has the beneficial effect of sanitizing products that incorporate the anti-microbial composition.

The anti-microbial composition of the invention typically is also able to break down biofilms that have already formed. It seems that the composition of the invention achieves this by dispersing the biofilms and effectively spreading out the cell walls so as to cause them to break down. The composition may also cause thinning and distortion of the biofilm, which makes the biofilm more susceptible to the anti-microbial agents and, therefore, increases the effectiveness of the anti-microbial agents in the composition.

As the anti-microbial composition of the invention physically disrupts the adhesion and attachment of a microorganism to a surface, which is a feature that is common to a wide range of microorganisms, including bacteria, fungi and moulds, the composition is effective against a broad range of microorganisms. Thus, an advantage of the anti-microbial composition of the invention is that it is able to prevent a broad range of microorganisms from adhering and attaching to the surface and, therefore, from forming a biofilm. Large numerous colonies are also substantially prevented from forming. Thus, the ability of the colony to grow is substantially reduced or even prevented. The anti-microbial composition of the invention is, therefore, general in its control of microorganisms.

It seems that as well as preventing the growth of colonies, the anti-microbial composition of the invention increases the relative age of the colony because new microorganisms are prevented from being produced. Thus, the anti-microbial agents of the composition are brought into contact with "older" microorganisms that are more susceptible to anti-microbial agents than newer ones. The anti-microbial agents are, therefore, more effective at lower concentrations than those that are normally used. Thus, the composition of the invention increases the efficacy of the anti-microbial action of the anti-microbial agents compared to when they are used alone.

The anti-microbial composition of the invention can easily be incorporated into other materials, such as functional materials. When incorporated into such materials, these become anti-microbial in nature and the surface of the formulation will be modified so as to substantially prevent the microorganisms from adhering and attaching thereto.

Another advantage of the anti-microbial composition is that it need not comprise-combinations of materials that are highly toxic to mammals. The anti-microbial agents used in the anti-microbial compositions are typically well known and widely understood and tested anti-microbial agents. The efficacy of the known anti-microbial agents is amplified in the compositions of the invention. Therefore, anti-microbial agents that have a low toxicity can be used in the anti-microbial compositions. In contrast, new anti-microbial agents for known techniques of sanitization use "stronger", more toxic and/or little tested materials.

The anti-microbial composition of the invention also does not comprise materials that produce highly persistent residues or rinsates or products that contain heavy metals and their salts. Thus, there is a greatly reduced risk of long term hazards associated with the anti-microbial compositions.

The composition of the invention does not interfere with the biochemical reproductive pathways of the microorganisms it controls. The risk of resistance build up and the development of resistant strains is, therefore, highly unlikely.

The surface tension of the first compound is greater than that of the second compound and is preferably less than the surface tension of water at any specified temperature. Thus, the first compound can typically act to reduce the surface tension of water. The surface tension of the first compound is from 20 to 35 mN/m at 20° C.

The surface tension of the second compound is from 8 to 14 mN/m at 20° C., more preferably 10 mN/m at 20° C. The low surface tension of the second compound reduces non-specific bonding with other components of the composition, particularly bonding with aqueous or hydrated materials.

The first compound is preferably hydrophobic. The second compound is preferably hydrophilic. This appears to provide a composition that is typically stable in both hydrophobic and hydrophilic materials. Additionally, the hydrophobic first compound typically attracts the hydrophilic second compound, so as to provide the desired opposing surface tension effects. This combination of properties is thought to create a microscopic turbulent effect that is disruptive to the formation of a biofilm. The fact that this effect is microscopic means that it has a great efficacy on microorganisms but not on larger macroorganisms.

Whilst it is preferred that the first compound is hydrophobic and the second compound is hydrophilic, it is possible for the first compound to be hydrophilic and the second compound to be hydrophobic.

Preferably, the first compound is a second anti-microbial agent. Thus, as well as contributing to the surface effects, the first compound also acts as an anti-microbial agent. However, the efficacy of the second anti-microbial agent is improved by the inclusion of the other components of the composition.

By the term "anti-microbial agent" we mean any chemical substance that can destroy microorganisms.

The first and second anti-microbial agents (hereinafter referred to generally as the anti-microbial agents) present in the compositions of the invention are typically well known and have been subject to research by the regulatory authorities. The anti-microbial agents generally have some effect when they are used alone. However, the efficacy of the anti-microbial agents is amplified when they are used in combination with the other components of the compositions of the invention.

Preferably, the composition of the invention comprises two or more anti-microbial agents. A typical composition may comprise four anti-microbial agents.

The anti-microbial agents are preferably of a polar nature. This enables them to associate with the other components of the composition, for example by hydrogen bonding or non-chemical bonding. This association brings the anti-microbial agents into direct association with the microorganisms as the other components of the composition of the invention themselves associate with the microbial wall. Thus, the anti-microbial agents are effective at low concentrations. The anti-microbial agents are not thought to form a chemical bond with the first and second compounds.

Preferably, the composition comprises at least one anti-microbial agent selected from bacteriocidal, fungicidal, algicidal, yeasticidal and moldicidal agents. More preferably, the composition comprises bacteriocidal, fungicidal and moldicidal agents.

The first anti-microbial agent is preferably an amphoteric compound, an iodophore, a phenolic compound, a quaternary ammonium compound, a hypochlorite or a nitrogen based heterocyclic compound.

The second anti-microbial agent is preferably a surfactant, more preferably a quaternary ammonium compound. Both the first and second anti-microbial agents may each comprise a quaternary ammonium compound.

Preferably, the anti-microbial compositions of the invention comprise one or more quaternary ammonium compounds, phenolic compounds and nitrogen based heterocyclic compounds as the anti-microbial agent.

Quaternary ammonium compounds that are suitable for use in the invention include compounds of formula $R^1R^2R^3R^4N^+X^-$, in which one or two of the R groups are alkyl, optionally substituted by aryl or optionally interrupted by aryl or a heteroatom, such as oxygen, and the other R groups are the same or different and are $C_1$ to $C_4$ alkyl groups.

Preferred quaternary ammonium compounds include benzalkonium halides, aryl ring substituted benzalkonium halides, such as ethyl-substituted benzalkonium halides, and twin chain quaternary ammonium compounds, such as dialkyldimethyl ammonium compounds wherein the two non-methyl alkyl groups are selected from medium and long chain alkyl groups, such as $C_8$ to $C_{12}$ alkyl, preferably octyl and dodecyl.

Suitable quaternary ammonium compounds in which an R group (i.e. $R^1$, $R^2$, $R^3$, $R^4$) contains a heteroatom include domiphen bromide, benzalkonium chloride and methylbenzalkomium chloride.

Other quaternary ammonium compounds suitable for use in the anti-microbial composition include alkylpyridinium compounds, such as cetylpyridinium chloride, and bridged cyclic amino compounds such as the hexaminium compounds.

Particularly preferred quaternary ammonium compounds include benzenemethanaminium N-dodecyl-N,N-dimethylchloride, benzenemethanaminium N-dodecyl-N,N-dimethyl-N-tetradecylchloride and benzyl-$C_{12}$-$C_{16}$-alkyldimethyl-ammoniumchloride.

Amphoteric compounds suitable for use in the present invention include long chain N-alkyl derivatives of amino acids. Long chain N-alkyl derivatives of glycine, alanine and beta-amino butyric acid are preferred. Particularly preferred compounds include dodecyl beta-alanine, dodecyl beta-aminobutyric acid, dodecylamino-di(aminoethylamino)glycine and N-(3-dodecylamino)propylglycine.

By the term "iodophores" we mean complexes of iodine or triiodine with a carrier, such as a neutral polymer. The carrier typically increases the solubility of iodine in water, provides a sustained release of the iodine and reduces the equilibrium concentrations of free iodine.

Suitable polymeric carriers from which iodophores can be prepared include polyvinylpyrrolidone, polyether glycols such as polyethylene glycols, polyvinyl alcohols, polyacrylates, polyamides, polyalkylenes and polysaccharides.

Suitable phenolic compounds include methyl, ethyl, butyl, halo and aryl substituted phenol. Preferred phenolic compounds include 2-phenylphenol, 2-benzyl-4-chlorophenol, 2-cyclopentanol-4-chlorophenol, 4-t-amylphenol, 4-t-butylphenol, 4-chloro-2-pentylphenol, 6-chloro-2-pentylphenol, p-chloro-meta-xylenol, 2,4,4-trichloro-2-hydroxydiphenol, thymol, 2-i-propyl-3-methylphenol, chlorothymol, 3-methyl-4-chlorophenol, 2,6-dichloro-4-n-alkyl phenols, 2,4-dichloro-meta-xylenol, 2,4,6-trichlorophenol and 2-benzyl-4-chlorophenol.

Suitable hypochlorites include alkali metal and alkaline earth metal hypochlorites, such as the hypochlorites of lithium, sodium, potassium and calcium. Other suitable hypochlorites include chlorinated trisodium phosphate and their various hydrates. Other suitable chlorine containing or chlorine releasing agents include chlorine dioxide and its precursors, as well as N,N-dichloro-4-carboxybenzenesulponamide (halazone), 1,3-dichloro-5,5-dimethylhydantoin (halane) and various chloroisocyanuric acid derivatives.

Suitable nitrogen based heterocyclic compounds include pyridine derivatives, such as 4-pyridine carboxylic acid hydrazide, sodium 2-pyridinethiol-1-oxide and bis-(2-pyridylthio)zinc-1,1-dioxide, triazoles, thiazoles and imidazoles.

A particularly preferred anti-microbial composition comprises benzenemethanaminium N-dodecyl-N,N-dimethylchloride, benzenemethanaminium N-dodecyl-N,N-dimethyl-N-tetradecylchloride, benzyl-$C_{12}$-$C_{16}$-alkyldimethyl-ammoniumchloride, 2-phenylphenol, 2-octyl-2H-isothiazol-3-one, 5-chloro-2-methyl-2H-isothiazol-3-one and 2-methyl-2H-isothiazol-3-one.

The particular anti-microbial agents selected for use in the composition will vary depending upon the environment in which the composition is intended to be used.

The second compound is preferably chemically inert and has a structure that attaches to virtually any substrate. The second compound can, therefore, remain at a surface for long periods of time. This means that the composition of the invention can easily be recharged.

The second compound is also capable of associating with the other components of the composition of the invention by means of non-chemical bonds and typically can adhere to and attract a wide range of polar materials including various anti-microbial agents.

The second compound is preferably a surfactant or oil, more preferably a short chain surfactant or oil. By the term "short chain" we mean $C_{12}$ to $C_{20}$. Suitable second compounds include silanes, polyethylene glycol, sodium lauryl sulphate, soya lecathin and preferably siloxanes such as polysiloxanes or silicones.

A preferred second compound is polydimethylsiloxane and a particularly preferred second compound is polydimethylhydroxysiloxane. For example, a polydimethylhydroxysiloxane having a viscosity of from 100 to 400 centistokes may be included in the compositions of the invention.

Preferably, the composition comprises from 1 to 4% by volume of the second compound; however other proportions are possible and lie within the scope of the invention.

Suitable polar solvents for use in the composition include water, alcohols, esters, hydroxy and glycol esters, polyols and ketones. It seems that the polar solvent helps to provide a composition that is stable and does not separate out into its various components.

Preferred alcohols for use in the composition include straight or branched chain $C_1$ to $C_5$ alcohols, particularly methanol, ethanol, propanol, iso-propanol, n-butanol, sec-butanol, tert-butanol, iso-butanol, 2-methyl-1-butanol, 1-pentanol and amyl alcohol (mixture of isomers).

Preferred esters for use in the composition include methyl acetate, ethyl acetate, n-propyl acetate, iso-propyl acetate, n-butyl acetate, iso-butyl acetate, sec-butyl acetate, amyl acetate (mixture of isomers), methylamyl acetate, 2-ethylhexyl acetate and iso-butyl isobutyrate.

Preferred hydroxy and glycol esters for use in the composition include methyl glycol acetate, ethyl glycol acetate, butyl glycol acetate, ethyl diglycol acetate, butyl diglycol acetate, ethyl lactate, n-butyl lactate, 3-methoxy-n-butyl acetate, ethylene glycol diacetate, polysolvan O, 2-methylpropanoic acid-2,2,4-trimethyl-3-hydroxypentyl ester, methyl glycol, ethyl glycol, isopropyl glycol, 3-methoxybutanol, butyl glycol, iso-butyl glycol, methyl diglycol, ethyl diglycol, butyl diglycol, isobutyl diglycol, diethylene glycol, dipropylene glycol, ethylene glycol monohexyl ether and diethylene glycol monohexyl ether.

Preferred polyols for use in the composition include ethylene glycol, propylene glycol, 1,3-butylene glycol, 1,4-butylene glycol, hexylene glycol, diethylene glycol, triethylene glycol and dipropylene glycol.

Preferred ketones for use in the composition include isobutyl heptyl ketone, cyclohexanone, methyl cyclohexanone, methyl isobutenyl ketone, pent-oxone, acetyl acetone, diacetone alcohol, isophorone, methyl butyl ketone, ethyl propyl ketone, methyl isobutyl ketone, methyl amyl ketone, methyl isoamyl ketone, ethyl butyl ketone, ethyl amyl ketone, methyl hexyl ketone, diisopropyl ketone, diisobutyl ketone, acetone, methyl ethyl ketone, methyl propyl ketone and diethyl ketone.

Particularly preferred polar solvents for use in the composition include isopropanol, diethylene glycol and dipropylene glycol.

Preferably, the composition comprises from 1 to 70% by volume of the polar solvent, but since the primary purpose of the solvent is dilution virtually any proportion of polar solvent is believed to be possible within the scope of the invention.

An especially preferred anti-microbial composition comprises 32% by volume of a mixture of benzenemethanaminium N-dodecyl-N,N-dimethylchloride and benzenemethanaminium N-dodecyl-N,N-dimethyl-N-tetradecylchloride (2.33:1), 6.0% by volume of a mixture of benzyl-$C_{12}$-$C_{16}$-alkyldimethyl-ammoniumchloride and 2-phenylphenol (2:1), 6.0% by volume of 2-octyl-2H-isothiazol-3-one, 16.0% by volume of a mixture of 5-chloro-2- methyl-2H-isothiazol-3-one and 2-methyl-2H-isothiazol-3-one (3:1), 1.0% by volume of a blend of polysiloxanes and balance by volume isopropanol.

Another especially preferred anti-microbial composition comprises 32% by volume of a mixture of benzenethanaminiumn N-dodecyl-N,N-dimethylchloride and benzenethanaminiumn N-dodecyl-N,N-dimethyl-N-tetradecylchloride (2.33:1), 6.0% by volume of a mixture of benzyl-$C_{12}$-$C_{16}$-alkyldimethyl-ammoniumchloride and 2-phenylphenol (2:1), 6.0% by volume of 2-octyl-2H-isothiazol-3-one, 16.0% by volume of a mixture of 5-chloro-2-methyl-2H-isothiazol-3-one and 2-methyl-2H-isothiazol-3-one (3:1), 1.0% by volume of polydimethylhydroxysiloxane and balance by volume isopropanol.

Another especially preferred anti-microbial composition comprises 5.0% by volume of a mixture of benzenethanaminiumn N-dodecyl-N,N-dimethylchloride and benzenethanaminiumn N-dodecyl-N,N-dimethyl-N-tetradecylchloride (2.33:1), 5.0% by volume of a mixture of benzyl-$C_{12}$-$C_{16}$-alkyldimethyl-ammoniumchloride and 2-phenylphenol (2:1), 12.0% by volume of 2-octyl-2H-isothiazol-3-one, 32.0% by volume of a mixture of 5-chloro-2-methyl-2H-isothiazol-3-one and 2-methyl-2H-isothiazol-3-one (3:1), 1.0% by volume of a blend of polysiloxanes and balance by volume diethyleneglycol.

A further especially preferred anti-microbial composition comprises 6.0% by volume of a mixture of benzenethanaminiumn N-dodecyl-N,N-dimethylchloride and benzenethanaminiumn N-dodecyl-N,N-dimethyl-N-tetradecylchloride (2.33:1), 6.0% by volume of a mixture of benzyl-$C_{12}$-$C_{16}$-alkyldimethyl-ammoniumchloride and 2-phenylphenol (2:1), 16.0% by volume of 2-octyl-2H-isothiazol-3-one, 32.0% by volume of a mixture of 5-chloro-2-methyl-2H-isothiazol-3-one and 2-methyl-2H-isothiazol-3-one (3:1), 1.0% by volume of a blend of poylsiloxanes and balance by volume isopropanol.

Yet another especially preferred anti-microbial composition comprises 6.0% by volume of a mixture of benzenemethanaminium N-dodecyl-N,N-dimethylchloride and benzenemethanaminium N-dodecyl-N,N-dimethyl-N-tetradecylchloride (2.33:1), 6.0% by volume of a mixture of benzyl-$C_{12}$-$C_{16}$-alkyldimethyl-ammoniumchloride and 2-phenylphenol (2:1), 16.0% by volume of 2-octyl-2H-isothiazol-3-one, 32.0% by volume of a mixture of 5-chloro-2-methyl-2H-isothiazol-3-one and 2-methyl-2H-isothiazol-3-one (3:1), 1.0% by volume of a blend of polysiloxanes and balance by volume dipropyleneglycol.

According to a further aspect of the invention, there is provided a formulation comprising an anti-microbial composition and at least one other functional material.

Suitable functional materials include plastics, fibres, coatings, films, laminates, adhesives, sealants, clays, china, ceramics, concrete, sand, paints, varnishes, lacquers, cleaning agents or settable or curable compositions such as fillers, grouts, mastics and putties.

The plastics may be in the form of films, sheets, stabs and molded plastic parts. Suitable plastics materials may be prepared from polyesters such as polyethylene terephthalate, polybutylene terephthalate, polyamides such as Nylon, polyimides, polypropylene, polyethylene, polybutylenes, polymethylpentene, polysiloxane, polyvinyl alcohol, polyvinylacetate, ethylene-vinylacetate, polyvinyl chloride, polyvinylidene chloride, epoxy, phenolic and polycarbonate cellulosics, cellulose acetate, polystyrene, polyurethane, acrylics, polymethyl methacrylate, acrylonitrile, butadiene-styrene copolymer, acrylonitrilestyrene-acrylic copolymers, acetals, polyketones, polyphenylene ether, polyphenylene sulfide, polyphenylene oxide, polysulfones, liquid crystal polymers and fluoropolymers, amino resins, thermo plastics, elastomers, rubbers such as styrene butadiene rubber and acrylonitrile butadiene rubber, polyacetal (polyoxymethylene), and blends and copolymers thereof.

Formulations comprising the anti-microbial composition and a plastics material as the functional material may, for example, be used to form products such as automobile parts, shower curtains, mats, protective covers, tape, packaging, gaskets, waste containers, general purpose containers, brush handles, sponges, mops, vacuum cleaner bags, insulators, plastic film, indoor and outdoor furniture, tubing, insulation for wire and cable, plumbing supplies and fixtures, siding for housing, liners, non-woven fabrics, kitchen and bathroom hardware, appliances and equipment, countertops, sinks, flooring, floor covering, tiles, dishes, conveyer belts, footwear including boots, sports equipment and tools.

Suitable fibres may be prepared from acetate, polyester such as PET and PTT, polyolefins, polyethylene, polypropylene, polyamides such as Nylon, acrylics, viscose, polyurethane, and Rayon, polyvinyl alcohol, polyvinyl chloride, polyvinylidene chloride, polysaccharide, and copolymers and blends thereof.

Formulations comprising the anti-microbial composition and a fibre as the functional material may, for example, be used in applications such as mattress cover pads and filling, pillow covers, sheets, blankets, fiberfill for quilts and pillows, curtains, draperies, carpet and carpet underlay, rugs, upholstery, table cloths, napkins, wiping cloths, mops, towels, bags, wall covering fabrics, cushion pads, sleeping bags and brush bristles. The fibres are also suitable for use in automotive and truck upholstery, carpeting, rear decks, trunk liners, convertible tops and interior liners. Furthermore, the fibres are suitable for use in umbrellas, outerwear, uniforms, coats, aprons, sportswear, sleepwear, stockings, socks, hosiery caps, and undergarment and inner liners for jackets, shoes, gloves and helmets, trim for outerwear and undergarments as well as brush bristles, artificial leather, filters, book covers, mops, cloth for sails, ropes, tents, and other outdoor equipment, tarps and awnings.

Coatings suitable for use in the formulations include waterborne, solvent-borne, 100% solids and/or radiation cure coatings. The coatings may be liquid or powder coatings.

Suitable coatings, films and laminates include alkyds, amino resins, such as melamine formaldehyde and urea formaldehyde, polyesters, such as unsaturated polyester, PET, PBT, polyamides such as Nylon, polyimides, polypropylene, polyvinylacetate, ethylene-vinylacetate, polyvinyl chloride, polyvinylidene chloride, epoxy, phenolic and polycarbonate cellulosics, cellulose acetate, polystyrene, polyurethane, acrylics, polymethyl methacrylate, acrylonitrile-butadiene-styrene copolymer, acrylonitrile-styreneacrylic copolymers, acetals, polyketones, polyphenylene ether, polyphenylene sulfide, polyphenylene oxide, polysulfones, liquid crystal polymers and fluoropolymers, thermoplastic elastomers, rubbers such as styrene butadiene rubber, acrylonitrile butadiene rubber, polyacetal (polyoxymethylene), and blends and copolymers thereof.

Formulations comprising the anti-microbial composition and coatings as the functional material may, for example, be used on walls, wall boards, floors, concrete, sidings, roofing shingle, industrial equipment, natural and synthetic fibres and fabrics, furniture, automotive and vehicular parts, packaging, paper products (wall coverings, towels, book covers) barrier fabrics, and glazing for cement tile and for vitreous china used in plumbing fixtures such as toilets, sinks, and countertops.

Adhesives and sealants suitable for use in the formulations include hot-melt, aqueous, solvent borne, 100% solids and radiation cure adhesives and sealants.

Suitable adhesives and sealants include alkyds, amino resins such as melamine formaldehyde and urea formaldehyde, polyesters such as unsaturated polyester, PET, PBT, polyamides such as Nylon, polyimide polypropylene, polyethylene, polybutylene, polymethylpentene, polysiloxane, polyvinyl alcohol, polyvinylacetate, ethylene-vinylacetate, polyvinyl chlorides such as plastisol, polyvinylidene chloride, epoxy, phenol and polycarbonate, cellulosics, cellulose acetate, polystyrene, polyurethane, acrylics, polymethylmethacrylate, acrylonitrile-butadienestyrene copolymer, acrylonitrile-styrene-acrylic copolymers, acetals, polyketones, polyphenylene ether, polyphenylene sulfide, polyphenylene oxide, polysulfones, liquid crystal polymers and fluoropolymers, thermoplastic elastomers, rubbers (including styrene butadiene rubber, acrylonitrile butadiene rubber, CR), polyacetal (polyoxymethylene), and blends and copolymers thereof.

Formulations comprising the anti-microbial composition and an adhesive or sealant as the functional material may, for example, be used in the manufacture of wood and plastic composites, adhesives for ceramic tiles, wood, paper, cardboard, rubber and plastic, glazing for windows, grout, sealants for pipes, adhesives, sealants and insulating materials for appliances, bathrooms, showers, kitchens, and construction.

Formulations comprising the anti-microbial composition and clay, china, ceramics, concrete, sand or grout as the functional material may, for example, be used in toilets, sinks, tile, flooring, stucco, plaster, cat litter, drainage and sewerage pipe.

The anti-microbial composition can be combined into a very wide variety of functional compounds for the manufacturing, contracting and construction industries. The nature of the anti-microbial composition may be varied according to the particular functional compounds and the number and nature of microorganisms present in the particular functional compound or environment in which it is used.

The formulation preferably comprises from 0.1 wt % to 5.0 wt %, more preferably from 0.1 to 4.0 wt %, even more preferably from 0.5 wt % to 2.0 wt %, of the anti-microbial composition.

The anti-microbial composition is highly effective against a broad range of microorganisms even when it is combined with another functional material to provide the formulation of the invention. The formulation can, optionally, be applied to a surface. The formulation provides long-term anti-microbial action, in both dry and damp conditions at the surfaces treated or in which the material is combined. This will lead to a sanitisation of the surfaces so that the surfaces and products will prevent the rapid replication of microbial species and, thus, substantially reduce the risks of contamination and infection.

The anti-microbial composition is mobile through most functional materials in which it is incorporated in the formulations of the invention. This is due to the presence of surfactant materials and oils and molecules of short chain length. In order to maintain this mobility, the surfactant materials and oils preferably have a carbon chain length of no greater than 20.

The anti-microbial composition tends to migrate across a concentration gradient and moves to the surface of products into which it has been incorporated. This is similar to the behaviour of plasticiser in polymers.

Both the anti-microbial composition and the formulation typically begin to dissociate into their component parts when they have been in continuous contact with water for longer than six to eight hours. The anti-microbial action, of the anti-microbial composition and the formulation, is substantially reduced once the composition and formulation have dissociated into their component parts. The components can then act as a carbon source or nutrient for many species of microorganisms. Thus, the anti-microbial composition and the formulation can degrade when submersed in water, to provide a rinsate/leachate of low toxicity and which has a short residence time in the environment.

It is thought that the rinsates have a low toxicity because the anti-microbial agents are associated with the second compound and so the composition does not readily dissociate in the presence of water.

The formulation can be designed so that it is stable and effective in most manufacturing environments. The formulation is typically stable up to temperatures of 200° C.

The property of mobility of the product permits materials that are highly frequently washed or rinsed to be "recharged" with the anti-microbial composition during a routine act of cleaning or maintenance.

Typically, the anti-microbial composition is incorporated into a simple conventional detergent solution or added to a "final rinse" during cleaning. The anti-microbial composition will be drawn, due to the presence of its hydrophobic elements, into the surface of the product to be "recharged". The sanitization properties of the formulation are, therefore, restored without the need for re-manufacture or difficult treatment processes.

Any wash off or rinsates containing the anti-microbial composition or formulation diluted by such a re-charging solution and water would quickly dissociate into the biodegradable components as previously discussed.

According to a further aspect of the invention, there is provided the use of an anti-microbial composition to prevent the formation of colonies of microorganisms on a surface at which it is provided.

According to yet a further aspect of the invention, there is provided the use of a formulation to prevent the formation of colonies of microorganisms on a surface at which it is provided.

The anti-microbial composition and formulation have an anti-bacterial effect against a wide range of gram-positive and gram-negative bacteria.

For example, they are effective against the following:
*Bacillus* species, such as *Bacillus subtilis, Bacillus cereus*
*Brevibacterium* species
*Brucella* species, such as *Brucella abortus*
*Lactobacillus* species
*Proteus vulgaris*
*Pseudomonas aeruginosa*
*Salmonella* species
*Staphylococcus* species, such as Methicillin Resistive *Staphylococcus Aureus* (MRSA)
*Streptococcus* species
*Flavobacterium* species
*Escherichia* species
*Aeromonas* species The anti-microbial composition and formulation also have activity against fungi and yeasts, such as:
*Penicillium* species
*Aspergillus niger*
*Cladosporium* species Fusarium species
Paecilomyces species
Streptomyces species
Saccharomyces species, such as S.cerevisiae
Monilia albicans The anti-microbial composition and formulation also have activity against certain species of algae such as:
Chlorella pyrenoidosa
Pleurococcus
Anabaena species According to another aspect of the invention, there is provided a method of manufacturing an anti-microbial composition, the method comprising the steps of (i) mixing the first compound and the first anti-microbial agent together, (ii) adding the second compound to the mixture of first compound and the first anti-microbial agent, (iii) adding the polar solvent to the mixture of the first and second compounds and the first anti-microbial agent and (iv) agitating the resulting mixture until a clear solution is formed.

According to yet a further aspect of the invention, there is provided a method of manufacturing a formulation, the method comprising the step of adding the anti-microbial composition to the functional compound.

The present invention is now illustrated but not limited with reference to the following examples.

EXAMPLE 1

Preparation of Anti-microbial Composition ("D4L")

A composition according to the present invention comprising components (a) to (f) in the amounts indicated was prepared:
(a) 32.0% by volume of a mixture of two benzalkonium chlorides (in a ratio of 2.33:1) i.e. benzenemethanaminium N-dodecyl-N,N-dimethylchloride and benzenemethanaminium N-dodecyl-N,N-dimethyl-N-tetradecyl-chloride (Trade Name: BAC-50m);
(b) 6.0% by volume of a mixture of benzyl-$C_{12}$-$C_{16}$-alkyldimethyl-ammoniumchloride (CAS no. 68424-85-1) and 2-phenyl phenol in the ratio 2:1 (Trade Name: Acticide 50X);
(c) 6.0% by volume of 2-octyl-2H-isothiazol-3-one (Trade Name: A-DW);
(d) 16.0% by volume of a mixture of 5-chloro-2-methyl-2H-isothiazol-3-one and 2-methyl-2H isothiazol-3-one in the ratio 3:1 (Trade Name: A-14);
(e) 1.0% by volume of polydimethylhydroxysiloxane (Trade Name: PD-D); and
(f) 39% by volume of an isopropanol blend (isopropanol, n-propanol and water to azeotropic limit about 1.0%).

Anti-microbial agents a, b, c and d were mixed together sequentially at room temperature following the sequence described above. The resulting mixture was then agitated thoroughly and the polysiloxane (e) was added to the mixture. The resulting mixture was agitated and isopropanol (f) was added. The mixture was then agitated until a clear solution was obtained.

The clear solution is referred to herein as "D4L".

EXAMPLE 2

Preparation of Anti-Microbial Composition ("LCF")

A composition according to the present invention comprising components (a) to (f) in the amounts indicated was prepared:
(a) 32.0% by volume of a mixture of two benzalkonium chlorides (in a ratio of 2.33:1) i.e. benzenemethanaminium N-dodecyl-N,N-dimethylchloride and benzenemethanaminium N-dodecyl-N,N-dimethyl-N-tetradecyl-chloride (Trade Name: BAC-50m);
(b) 6.0% by volume of a mixture of benzyl-$C_{12}$-$C_{16}$-alkyldimethyl-ammoniumchloride (CAS no. 68424-85-1) and 2-phenyl phenol in the ratio 2:1 (Trade Name: Acticide 50X);
(c) 6.0% by volume of 2-phenyl phenol;
(d) 16.0% by volume of a 25% solution of 1,2-benziothiazolin-3-one in isopropanol;
(e) 1.0% by volume of polydimethylhydroxysiloxane (Trade Name: PD-D); and
(f) 39% by volume of an isopropanol blend (isopropanol, n-propanol and water to azeotropic limit about 1.0%).

Anti-microbial agents a, b, c and d were mixed together sequentially at room temperature following the sequence described above. The resulting mixture was then agitated thoroughly and the polydimethylhydroxysiloxane (e) was added to the mixture. The resulting mixture was agitated and isopropanol (f) was added. The mixture was then agitated until a clear solution was obtained. The clear solution is referred to herein as "LCF".

EXAMPLE 3

Preparation of Detergent Formulation Comprising the Anti-microbial Agent Composition of Example 1 (i.e. D4L)

An amphoteric non-ionic detergent, such as washing-up liquid, having a pH of from 6 to 8, was diluted in water in a ratio of 1 part detergent to 25 parts of water by volume. To this solution was added between 0.5 and 2.0% by volume of the anti-microbial agent composition prepared according to Example 1 (i.e. D4L).

EXAMPLE 4

Effectiveness of Anti-microbial Agent Formulation Against *Escherichia coli, Staphylococcus aureus* and *Pseudomonas aeruginosa*

Method

Two samples were tested. These were a detergent formulation prepared according to Example 3 comprising 2% by volume of the anti-microbial agent composition of Example 1, and a neutral detergent. The neutral detergent was used as a standard reference.

A bacterial culture (0.1 ml) in a nutrient medium was applied to a previously sterilised petri dish over an area 7×5 cm. The bacterial culture was then allowed to dry for 30 minutes.

The inoculated area was then wiped with a test wipe soaked either in water or the test solution to contact the test fluid with the bacteria. The test solution was applied using either an absorbent cloth or an innoculum loop. The innoculated area was also left untreated to provide an "uncleaned control", in which the infected area was not washed or even wiped with water. The bacteria remaining on the surface of the petri dish were numerated after periods of 15 and 30 seconds.

The bacteria remaining on the surface of the petri dish were numerated by wetting a sterile swab in a sterile peptone solution (0.1%) and thoroughly rubbing the swab over the area to be sampled, turning the swab as it was rubbed over the appropriate area. The swab was then returned to a sterile tube; Ringers solution (5 ml, ¼ strength) was added; and the swab left for at least 10 minutes.

The swab tubes were plated out making serial decimal dilutions, using the Miles and Misra Total Viable Count Technique and incubated inverted at 37° C. overnight. The number of colony forming units (CFU) (taken to be viable bacterial individuals) was then counted.

Calculation

The log reduction in bacterial numbers was calculated compared to the water control and the uncleaned control.

The total number of CFUs per ml of neat sample was calculated for each test sample and the controls.

The log of the number of CFUs for the water control, or the uncleaned control, was calculated to give value A. This was repeated for the test anti-microbial composition to give value B.

A−B=Log Reduction (A=log CFUs water or uncleaned control, B=log CFU5 test sample)

A log reduction of greater than 4 is considered to be effective.

TABLE 1

Results

| Composition | Organism | Log reduction after 15 secs | Log reduction after 30 secs |
|---|---|---|---|
| Anti-microbial composition | Escherichia coli[a] | 1.0 | >4.0 |
| Anti-microbial composition | Staphylococcus aureus[b] | >4.9 | >4.9 |
| Anti-microbial composition | Pseudomonas aeruginosa[c] | 1.8 | 3.3 |

[a]Total viable count $6.8 \times 10^8$
[b]Total viable count $5.8 \times 10^8$
[c]Total viable count $1.5 \times 10^9$ Conclusions A 2% by volume solution of the anti-microbial composition gave a log reduction of 1.0 after 15 seconds and >4.0 after 30 seconds when tested against *Escherichia coli*.

A 2% by volume solution of anti-microbial composition gave a log reduction of >4.9 after 15 seconds when tested against *Staphylococcus aureus*.

A 2% by volume solution of anti-microbial composition gave a log reduction of 1.8 after 15 seconds and 3.3 after 30 seconds when tested against *Pseudomonas aeruginosa*.

EXAMPLE 5

Resistance of Painted Film Formulations Containing an Anti-microbial Composition to Dry Film Fungal and Algal Colonisation The following formulations comprising paint and the anti-microbial agent composition of Example 1 were tested:

| Composition Number | % by volume of Anti-microbial Composition |
|---|---|
| Control | 0.00% |
| 1 | 0.50% |
| 2 | 0.75% |
| 3 | 1.00% |
| 4 | 1.50% |
| 5 | 2.00% |

Method—Dry Film Fungal Resistance Test (Based on British Standard BS3900 Part G6)

Each formulation was painted onto 6×9 cm gypsum panels. Two coats of each formulation were painted onto the gypsum panels, allowing 24 hours drying time between each coat. When the panels were dry, they were spray inoculated with a mixed spore suspension prepared from fungi (including yeasts) isolated from or known to grow on painted surfaces. The test panels were suspended in a high humidity cabinet at 24° C. for four weeks and the resultant fungal growth assessed visually and microscopically. Fungal growth rating was according to BS3900 Part G6.

The micro-organisms used were:
Aspergillus versicolor
Aureobasidium pullulans
Cladosporium cladosporioides
Penicillium purpurogenum
Phoma violaceae
Rhodotorula rubra
Sporobolomyces roseus
Stachybotrys chartarum
Ulocladium atrum Method—Dry Film Algal Resistance Test—Vermiculite Bed Method Each formulation was painted onto 10×10 cm calcium silicate panels. Two coats of each formulation were painted onto the panels, allowing 24 hours drying time between each coat. When the panels were dry, they were weathered using a QUV Accelerated Weathering Tester for 125 hours using a water spray cycle. Each panel was then cut in half The half panels were placed in the surface of vermiculite (200 g) moistened with water (800 cm$^3$) in a transparent plastic box with a close fitting lid. The panels were each spray inoculated with a mixed algal suspension three times at intervals of two weeks and sprayed with water each week. The panels were incubated for 13 weeks at 20° C. and illuminated with 30 W daylight type fluorescent tubes (giving approximately 1000 lux) for 16 hours per day. The resultant algal growth was assessed visually and microscopically.

The microorganisms used were:
Chlorella emersonii
Gloeocapsa alpicola
Nostoc commune
Pleurococcus sp.
Stichococcus bacillaris
Stigeoclonium tenue
Trentepohlia aurea
Trentepohlia odorata Results

TABLE 2

Dry Film Fungal Resistance Test

| Composition Number | % Anti-microbial agent (by volume) | Observed Rating* (4 weeks) |
|---|---|---|
| Control | 0.00% | 4 (40+) |
| 1 | 0.50% | 3 (30+) |
| 2 | 0.75% | 2 (10+) |
| 3 | 1.00% | 2 (5+) |
| 4 | 1.50% | 2 (5+) |
| 5 | 2.00% | 0 (0) |

*Average rating of replicate panels given.

TABLE 3

Dry Film Algal Resistance Test

| Composition Number | % Anti-microbial agent (by volume) | Film Algal Growth- Replicate 1 | Rating/Intensity- Replicate 2 |
|---|---|---|---|
| Control | 0.00% | 4 (50+) | 4 (40+) |
| 1 | 0.50% | 3 (20+) | 3 (20+) |
| 2 | 0.75% | 2 (10+) | 3 (15+) |
| 3 | 1.00% | 2 (10+) | 2 (10+) |
| 4 | 1.50% | 2 (10+) | 2 (10+) |
| 5 | 2.00% | 2 (5+) | 2 (5+) |

Growth Ratings

The first figure represents the fungal growth cover as follows:
 0=No growth
 1=Trace growth
 2=1 to 10% Coverage of growth
 3=11 to 30% Coverage of growth
 4=31 to 70% Coverage of growth
 5=71 to 100% Coverage of growth The second figure in brackets represents the % cover and an assessment of the intensity rating, as follows:
 0=Growth barely visible to the naked eye
 +=Light growth
 ++=Moderate growth
 +++=Dense growth Conclusion The control sample (containing no anti-microbial composition) was found to be susceptible to dry film fungal and algal colonisation.

An addition of 1.0% of the anti-microbial composition was found to control the fungal and algal population to a level that meets the pass criterion, of below 20%.

EXAMPLE 6

Microbiological Testing Against MRSA of Coil Coating Panels Treated with the Anti-microbial Composition of Example 1

Coil coating panels, manufactured by Becker Industrial Coatings Ltd., Liverpool, were treated with a range of concentrations of an anti-microbial composition according to Example 1. The panels were then tested to demonstrate whether they have antibacterial properties against Methicillin Resistant *Staphylococcus Aureus* (MRSA).

The panels were coated as follows:

| | |
|---|---|
| S1 | Coil coating panel, 1.0% by volume anti-microbial composition |
| S2 | Coil coating panel, 1.5% by volume anti-microbial composition |
| S3 | Coil coating panel, 2.0% by volume anti-microbial composition |
| S4 | Coil coating panel, 2.5% by volume anti-microbial composition |
| S5 | Coil coating panel, 3.0% by volume anti-microbial composition |
| S6 | Coil coating panel, 0% anti-microbial composition (control) |

Method

MRSA culture was diluted to approximately $1.5 \times 10^4$ CFU/ml with sterile deionised water. 1 ml of this solution was placed on a coil coating panel and was continuously applied over an area of approximately 5 cm×5 cm using a hand held spreader for a contact period of 1 minute. The culture was immediately recovered from the panel using a swab and was transferred to a universal bottle containing neutralizer (1 ml) and maximum recovery diluent (9 ml). 10 fold serial dilutions were prepared and 0.1 ml aliquots of the dilutions were plated onto nutrient agar, in duplicate. The plates were incubated at 37° C. for 24 hours and 48 hours and read using conventional techniques.

The procedure was repeated with a culture contact time of 5 minutes. All six samples were subjected to the same test protocol.

TABLE 4

Results

| Sample | Contact time 1 min (CFU/ml) | Contact time 5 min (CFU/ml) |
|---|---|---|
| S1 | 82 | 55 |
| S2 | 73 | 50 |
| S3 | 60 | 38 |
| S4 | 55 | 35 |
| S5 | 49 | 30 |
| S6 | $1.1 \times 10^3$ | $2.5 \times 10^2$ |

Conclusion

All of the test samples (S1 to S5) produced very significant decreases in the bacterial count (from $1.5 \times 10^3$ CFU/ml) in 1 minute of contact time and further small decreases after 5 minutes. Total bacterial kill was not achieved in 5 minutes of contact.

The control sample (S6) produced a small decrease in the bacterial count (from $1.5 \times 10^3$ CFU/ml) in 1 minute of contact time, which may be primarily due to the difficulty of recovering the culture from the panels using swabbing techniques. After 5 minutes of contact time the control samples bacterial count had significantly decreased primarily due to the drying out of the culture during the continuous spreading action on the panels.

The coil coatings treated with the anti-microbial composition are effective, at all of the tested concentrations, in very significantly reducing the level of MRSA bacteria when in contact in an aqueous medium for short periods.

These coatings would be very effective in assisting in the control of MRSA bacterial contamination in hospitals and similar environment.

EXAMPLE 7

Microbiological Testing Against MRSA of HMG's Panels of Food Safe PVC 94 Laminate Treated with the Anti-microbial Composition of Example 1

Panels, from H. Marcel Guest Ltd (HMG), coated with food safe PVC 94 laminate were treated with a formulation comprising a paint and 2% by volume of the anti-microbial composition prepared according to Example 1 in order to demonstrate whether they have antibacterial properties against Methicillin Resistant *Staphylococcus Aureus* (MRSA).

Samples

| | |
|---|---|
| S1 | PVC 94 laminated panel, 2% by volume anti-microbial composition, Clear. |
| S2 | Control, Clear. |
| S3 | PVC 94 laminated panel, 2% by volume anti-microbial composition, White. |
| S4 | Control, White. |

Method

The MRSA culture was diluted to approximately $1.5 \times 10^4$ CFU/ml with sterile deionised water and 1 ml was placed on a panel and continuously applied over an area of approximately 5 cm×5 cm using a hand held spreader for a contact period of 1 minute. The culture was immediately recovered from the panel using a swab and was transferred to a universal bottle containing neutralizer (1 ml) and maximum recovery diluent (9 ml). 10 fold serial dilutions were prepared and 0.1 ml aliquots of the dilutions were plated onto nutrient agar, in duplicate. The plates were incubated at 37° C. for 24 hours and 48 hours and read using conventional techniques. The procedure was then repeated with a culture contact time of 5 minutes. All four samples were subjected to the same test protocol.

TABLE 5

Results

| Sample | Contact Time 1 min (CFU/ml) | Contact Time 5 min (CFU/ml) |
|---|---|---|
| S1 | 52 | 30 |
| S2 | $2.1 \times 10^2$ | $1.6 \times 10^2$ |
| S3 | 97 | 31 |
| S4 | $4.1 \times 10^2$ | $1.9 \times 10^2$ |

Discussion

The test samples (S1 and S3) produced very significant decreases in the bacterial count (from $1.5 \times 10^3$ CFU/ml) in 1 minute of contact time and further small decreases after 5 minutes. Total bacterial kill was not achieved in 5 minutes of contact.

The control samples (S2 and S4) produced significant but smaller decreases in the bacterial count (from $1.5 \times 10^3$ CFU/ml) in 1 minute and 5 minutes of contact time. This may be partially due to the difficulty of recovering the culture from the panels using swabbing techniques and to the drying out of the culture during the continuous spreading action on the panels.

Conclusions

The PVC 94 laminated panels treated with 2% by volume anti-microbial composition are effective in reducing the level of MRSA bacteria when in contact in an aqueous medium for short periods.

These coatings would be likely to be very effective in assisting in the control of MRSA bacterial contamination in hospitals and similar environment.

EXAMPLE 8

Determination of the Anti-microbial Effect of Coated Test Panels Containing the Anti-microbial Composition According to Example 1

The microorganisms tested were:

| Bacillus subtilis | NCTC 44878 | $3.2 \times 10^6$ CFU/ml |
|---|---|---|
| Pseudomonas aeruginosa | NCTC 10662 | $3.6 \times 10^6$ CFU/ml |

Method

Test panels were coated with paint/powder coatings containing the anti-microbial composition according to Example 1. The coated test panels were challenged with broth cultures of the two organisms at the above concentrations for 10 minutes contact time.

The bacterial suspension was pipetted onto the coated test panel and removed with a swab after 10 minutes. The swab was transferred to maximum recovery diluent and plated onto Standard Plate Count Agar, incubed at 30° C. for 24 hours and the total number of colonies counted.

Results

TABLE 6

Paint Coating

| Panel Number | Bacillus subtilis (CFU/ml) | Pseudomonas aeruginosa (CFU/ml) |
|---|---|---|
| 1 | 20 | 32 |
| 2 | 7 | 3 |
| 3 | TNC | TNC |
| 4 | 60 | 15 |
| 5 | 83 | 41 |
| 6 | TNC | TNC |

TABLE 7

Epoxy Polygloss Powder Coating

| Panel Number | Bacillus subtilis (CFU/ml) | Pseudomonas aeruginosa (CFU/ml) |
|---|---|---|
| 1 | TNC | TNC |
| 2 | TNC | 286 |
| 3 | TNC | 132 |
| 4 | 30 | 9 |
| 5 | 150 | 24 |
| 6 | 42 | 30 |

TABLE 8

Grey Epoxy Polyester Gloss Powder Coating

| Panel Number | Bacillus subtilis (CFU/ml) | Pseudomonas aeruginosa (CFU/ml) |
|---|---|---|
| 1 | 4 | 13 |
| 2 | 10 | 9 |
| 3 | 6 | 5 |
| 4 | TNC | TNC |
| 5 | TNC | TNC |

TNC = Too numerous to count

Conclusion

The results show that the bacteria are almost completely eradicated within 10 minutes contact time by the anti-microbial composition according to Example 1 in many of the paint/powder coating formulations, even though the surface is dry.

A powder coating containing the anti-microbial composition according to Example 1 at the concentrations shown to be effective is, therefore, likely to be highly effective in reducing the number of bacteria on a surface in a short timescale.

EXAMPLE 9

Effectiveness of the Anti-microbial Composition "LCF" of Example 2

The samples tested were as follows:

| | |
|---|---|
| 1000 LCF: | 1% by volume LCF in water |
| 2000 LCF: | 2% by volume LCF in water |
| 3000 LCF: | 3% by volume LCF in water |

The microorganisms used were:

Legionella pneumophila NCTC 11192
Escherichia coli NCTC9001
Staphylococcus aureus NCIMB 12702
Salmonella enteritidis NCTC5188
Listeria monocytogenes Type 1 NCTC7973
Pseudomonas aeruginosa NCIMB 12469

Method

The European Suspension Test (Pr En 1276 November 1995) was conducted under the following experimental conditions:

| | |
|---|---|
| Test concentrations: | Neat |
| Test temperature: | 10° C. (+/−1° C.) |
| Test conditions: | Clean (0.3 g/100 ml bovine albumin) |
| | Dirty (3 g/100 ml bovine albumin) |
| Neutraliser: | Lecithin 3 g/l, polysorbate 80 30 g/l, sodium thiosulphate 5 g/l, L. histidine 1 g/l, saponin 30 g/l in diluent |
| Contact time: | 5 min |
| Temp of incubation: | 37° C. (+/−1° C.) |

Results

For the test results to be valid the neutraliser used must be shown to be non-toxic to the bacteria and to adequately neutralise the product under test. The experimental test conditions must also be validated.

To pass the test the product when diluted in hard water must demonstrate at least a $10^5$ reduction in viable count when tested under simulated clean or dirty conditions and under the required test conditions.

TABLE 9

Results for 1000 LCF

| Test Organisms | Clean Conditions Log Reduction | Pass/Fail | Dirty Conditions Log Reduction | Pass/Fail |
|---|---|---|---|---|
| L. pneumophila | 4.12 | FAIL | 3.94 | FAIL |
| E. coli | 4.26 | FAIL | 4.02 | FAIL |
| S. aureus | 4.08 | FAIL | 4.10 | FAIL |
| S. enteritidis | 4.44 | FAIL | 4.08 | FAIL |
| L. monocytogenes | 4.54 | FAIL | 4.20 | FAIL |
| P. aeruginosa | 4.02 | FAIL | 3.90 | FAIL |

TABLE 10

Results for 2000 LCF

| Test Organisms | Clean Conditions Log Reduction | Pass/Fail | Dirty Conditions Log Reduction | Pass/Fail |
|---|---|---|---|---|
| L. pneumophila | 4.68 | FAIL | 4.62 | FAIL |
| E. coli | 4.76 | FAIL | 4.34 | FAIL |
| S. aureus | 4.68 | FAIL | 4.22 | FAIL |
| S. enteritidis | 4.72 | FAIL | 4.28 | FAIL |
| L. monocytogenes | 4.86 | FAIL | 4.30 | FAIL |
| P. aeruginosa | 4.64 | FAIL | 4.10 | FAIL |

TABLE 11

Results for 3000 LCF

| Test Organisms | Clean Conditions Log Reduction | Pass/Fail | Dirty Conditions Log Reduction | Pass/Fail |
|---|---|---|---|---|
| L. pneumophila | 4.84 | FAIL | 4.68 | FAIL |
| E. coli | 4.72 | FAIL | 4.27 | FAIL |
| S. aureus | 4.84 | FAIL | 4.44 | FAIL |
| S. enteritidis | 4.92 | FAIL | 4.95 | FAIL |
| L. monocytogenes | 4.98 | FAIL | 4.54 | FAIL |
| P. aeruginosa | 4.79 | FAIL | 4.62 | FAIL |

Conclusion

All three samples, 1000 LCF, 2000 LCF and 3000 LCF, failed the European Suspension Test at 10° C. for all of the microorganisms used. However, although the samples failed this stringent test, they did display significant anti microbial activity against all of the organisms.

EXAMPLE 10

Effectiveness of the Anti-microbial Composition "D4L" of Example 1

The samples tested were as follows:

| | |
|---|---|
| 500 D4L: | 0.5% by volume D4L in water |
| 1000 D4L: | 1.0% by volume D4L in water |
| 1500 D4L: | 1.5% by volume D4L in water |
| 2000 D4L: | 2.0% by volume D4L in water |

The microorganisms used were:
Legionella pneumophila NCTC 11192
Escherichia coli NCTC9001
Staphylococcus aureus NCIMB 12702
Salmonella enteritidis NCTC5188
Listeria monocytogenes Type 1 NCTC7973
Pseudomonas aeruginosa NCIMB 12469

Method

The European Suspension Test was conducted under the following experimental conditions:

| | |
|---|---|
| Test concentrations: | Neat |
| Test temperature: | 10° C. (+/−1° C.) |
| Test conditions: | Clean (0.3 g/100 ml bovine albumin) |
| | Dirty (3 g/100 ml bovine albumin) |

-continued

| | |
|---|---|
| Neutraliser: | Lecithin 3 g/l, polysorbate 80 30 g/l, sodium thiosulphate 5 g/l, L. histidine 1 g/l, saponin 30 g/l in diluent |
| Contact time: | 5 min |
| Temp of incubation: | 37° C. (+/−1° C.) |

Results

For the test results to be valid the neutraliser used must be shown to be non-toxic to the bacteria and to adequately neutralise the product under test. The experimental test conditions must also be validated.

To pass the test the product when diluted in hard water must demonstrate at least a $10^5$ reduction in viable count when tested under simulated clean or dirty conditions and under the required test conditions.

TABLE 12

Results for 500 D4L

| Test Organisms | Clean Conditions Log Reduction | Pass/Fail | Dirty Conditions Log Reduction | Pass/Fail |
|---|---|---|---|---|
| L. pneumophila | 4.64 | FAIL | 4.48 | FAIL |
| E. coli | 4.76 | FAIL | 4.55 | FAIL |
| S. aureus | 4.80 | FAIL | 4.70 | FAIL |
| S. enteritidis | 4.82 | FAIL | 4.75 | FAIL |
| L. monocytogenes | 4.89 | FAIL | 4.72 | FAIL |
| P. aeruginosa | 4.50 | FAIL | 4.36 | FAIL |

TABLE 13

Results for 1000 D4L

| Test Organisms | Clean Conditions Log Reduction | Pass/Fail | Dirty Conditions Log Reduction | Pass/Fail |
|---|---|---|---|---|
| L. pneumophila | 6.10 | PASS | 5.64 | PASS |
| E. coli | 6.42 | PASS | 5.85 | PASS |
| S. aureus | 6.10 | PASS | 5.58 | PASS |
| S. enteritidis | 5.98 | PASS | 5.92 | PASS |
| L. monocytogenes | 6.72 | PASS | 6.27 | PASS |
| P. aeruginosa | 5.88 | PASS | 5.21 | PASS |

TABLE 14

Results for 1500 D4L

| Test Organisms | Clean Conditions Log Reduction | Pass/Fail | Dirty Conditions Log Reduction | Pass/Fail |
|---|---|---|---|---|
| L. pneumophila | 6.88 | PASS | 6.14 | PASS |
| E. coli | 7.14 | PASS | 7.02 | PASS |
| S. aureus | 6.98 | PASS | 6.34 | PASS |
| S. enteritidis | 6.52 | PASS | 6.40 | PASS |
| L. monocytogenes | 7.39 | PASS | 6.83 | PASS |
| P. aeruginosa | 6.45 | PASS | 6.06 | PASS |

TABLE 15

Results for 2000 D4L

| Test Organisms | Clean Conditions Log Reduction | Pass/Fail | Dirty Conditions Log Reduction | Pass/Fail |
|---|---|---|---|---|
| L. pneumophila | 7.22 | PASS | 6.48 | PASS |
| E. coli | 7.20 | PASS | 7.12 | PASS |
| S. aureus | 7.34 | PASS | 7.08 | PASS |
| S. enteritidis | 7.12 | PASS | 6.62 | PASS |
| L. monocytogenes | 7.59 | PASS | 7.36 | PASS |
| P. aeruginosa | 6.78 | PASS | 6.32 | PASS |

Conclusion

Three samples, 1000 D4L, 1500 D4L and 2000 D4L, passed the European Suspension Test at 10° C., for all of the microorganisms under test. Under identical conditions 500 D4L failed the test.

A comparison of the results of the tests of Examples 9 and 10 shows that the composition "D4L" is more effective than the composition "LCF". The composition "D4L" includes anti-microbial agents that are more polar than those included in the composition "LCF". Thus, the inclusion of polar anti-microbial agents increases the efficacy of the composition.

EXAMPLE 12

The Dissociation of the Anti-microbial Composition "D4L" of Example 1 Upon Immersion in Water This Example was conducted to assess the difference in biofilm growth between experimental and control surfaces after 48 hours submersion in water. The experimental surfaces were coated with the anti-microbial composition but the control surfaces were not.

Method

Eight aluminum bottles were painted with four different paint types. The paint types were Series 1 to 4, as set out below. Four of the bottles were painted with paint including 2% by weight of the anti-microbial composition of Example 1 and four were painted with standard paint and used as controls.

The paint types were as follows:

| | |
|---|---|
| Series 1: | K Type Gloss (tough, durable enamel for high quality industrial finishing and decorative interior/exterior woods). |
| Series 2: | Matt White Emulsion (interior/exterior decorative duties. Contains a preservative for in can protection against microbial spoilage). |
| Series 3: | Blue Hydracoat (waterborne alternative to alkyd synthetic enamels used for toy and model coating). |
| Series 4: | Aquaguard (two pack epoxy coatings for walls and floors). |

Each bottle was placed into an inoculated solution, covered and incubated for 48 hours. The bottles were then removed and sprayed with 0.5% Tween/phosphate buffer solution (100 ml) to remove any biofilm that had formed. The resulting solutions were plated out making serial decimal dilutions, using the Miles and Misra Total Viable Count Technique and incubated inverted at 37° C. overnight. The number of colony forming units (CFU) (taken to be viable bacterial individuals) was then counted and the experimental plates were compared to the controls.

Results

Biofilm growth recovered after 24 hours—*E. coli*

| | |
|---|---|
| Series 1: | 50% more growth on experimental, compared to the control. |
| Series 2: | No growth on experimental, very small growth on control. |
| Series 3: | 25% more growth on experimental, compared to control. |
| Series 4: | 43% more growth on experimental, compared to the control. |

Biofilm growth recovered after 24 hours—*Pseudomonas aeruginosa*

| | |
|---|---|
| Series 1: | 50% more growth on experimental, compared to the control. |
| Series 2: | No growth on control, very small growth on experimental. |
| Series 3: | 25% more growth on experimental, compared to control. |
| Series 4: | 20% more growth on experimental, compared to the control. |

Conclusion

The components of the anti-microbial compositions dissociate and dissolve in the surrounding solution and provide a carbon source for the microbial populations. The results show an increase in growth of microorganisms on the treated materials after 24 hour immersion in microbial broth. This indicates a more nutrient rich environment in the paints including the anti-microbial composition of the invention compared to the controls and shows that the anti-microbial composition is biodegradable.

EXAMPLE 13

Low Rinsate Toxicology

Method

Four different surface coatings, paint series 1 to 4 as described in Example 12, were applied to aluminum panel substrates. These were then compared to controls that did not include the anti-microbial composition.

The microorganisms used were *E. coli* and *Pseudomonas aerogenosa*.

After 24 hours, the panels were rinsed with deionised water and the washings tested using Microtox Testing. This test uses a photoluminescent vibrio sp. (a bioluminous microbe) that is highly responsive to the effect of toxins. In the Microtox Test, a sample is mixed with living bacteria that are sensitive to the presence of toxic compounds. The mixture is allowed to regulate for a short time and then a light reading is taken. In the presence of substances at concentrations that are acutely toxic and which pose harm to humans, the bacteria are impaired and cease to give off light. Thus, the greater the light loss from a sample, the more toxic it is.

Results

Figure 2:
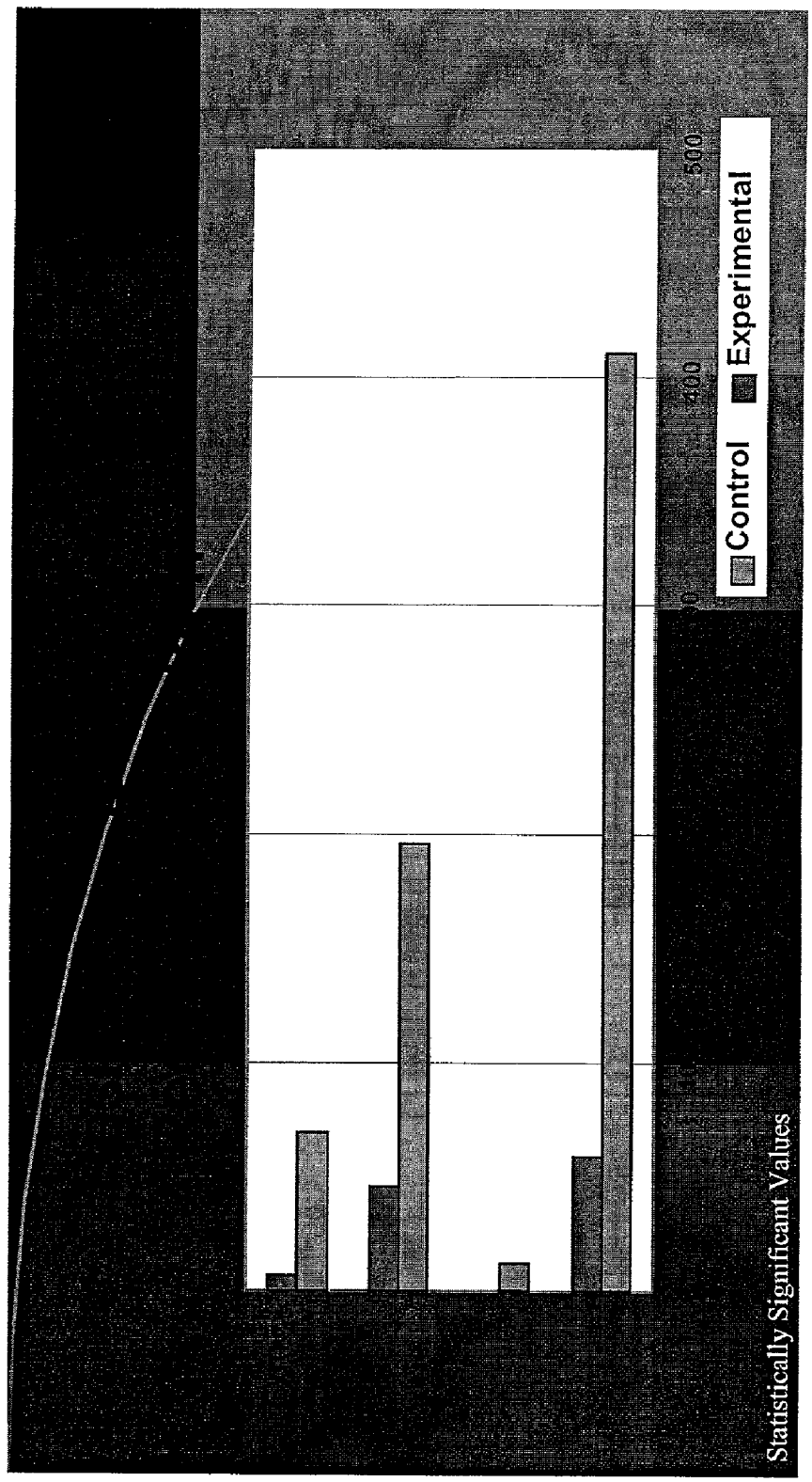
FIG. 2 illustrates the residual *E. coli* biofilm recovered after 24 hours for the experimental and control samples.

FIGS. 1 and 2 show the residual *P. aeruginosa* and *E. coli* biofilm recovered after 24 hours, for the experimental and control samples respectively. It is clear from FIGS. 1 and 2 that the biofilm formation is greater for the control samples.

Figure 3:
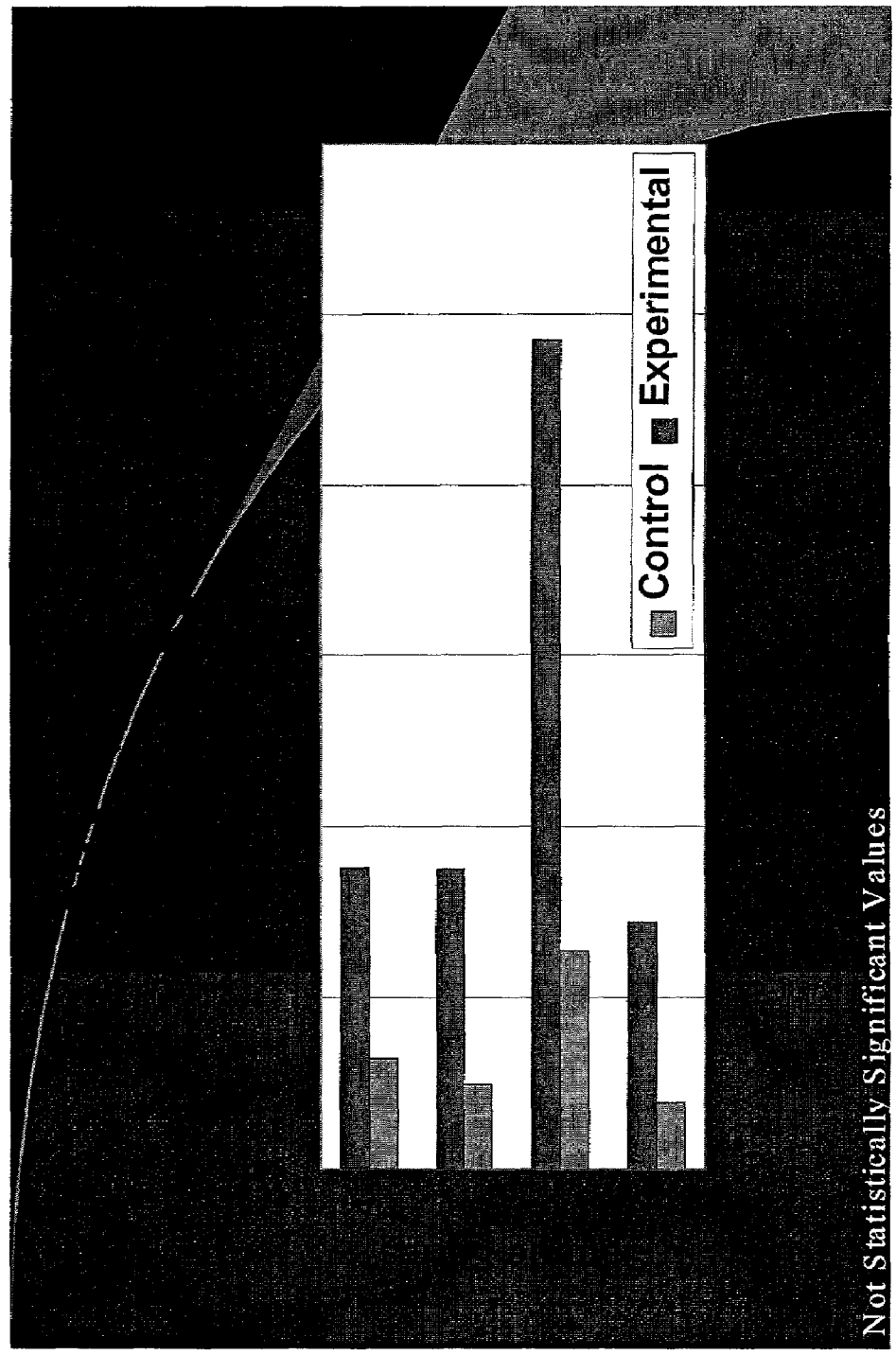
FIG. 3 illustrates the toxicity of the surface rinsates for *P. aeruginosa* for the experimental and control samples.
Figure 4:
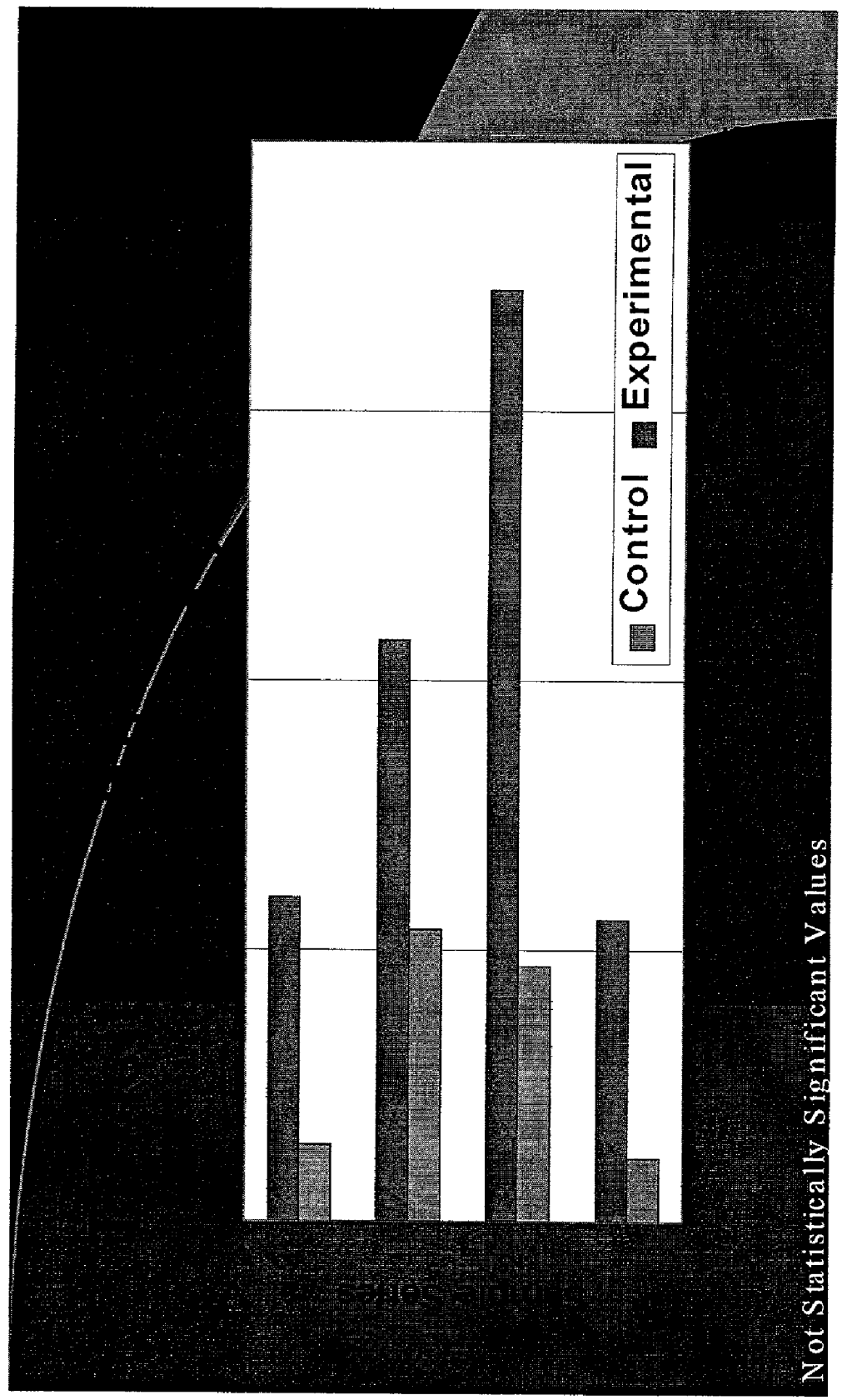
FIG. 4 illustrates the toxicity of the surface rinsates for *E. coli* for the experimental and control samples.

FIGS. 3 and 4 show the toxicity of the surface rinsates for *P. aeruginosa* and *E. coli*, for the experimental and control samples respectively. Rinsates for the control samples are less toxic than for the experimental samples. However, the rinsates for both the experimental and the control samples showed low toxicity.

Values for the effective concentration at which 50% of the population suffers from some adverse effect (EC50) were difficult to calculate and values for the lethal dose 50 (LD50) were not calculable.

The rinsate of some of the anti-microbial compositions was similar in effect to that of the control of other test paints. For example, paint series 1 including the anti-microbial composition had similar effect on the test as paint series 3 without the composition of the invention. Thus, different products of similar types (i.e. paints) have different results in the Microtox test on the rinsate. This indicates that the anti-microbial composition of the invention only has a small effect on the rinsate toxicology, which is within the normal range for products that do not include anti-microbial agents. Thus, the rinsate has low toxicity and is safe.

Low toxicity of rinsates from the compositions of the invention is highly desirable for the environment.

EXAMPLE 14

Anti-microbial Testing of Coated Panels

Steel panels with a coating containing 0% (as a control), 1.5%, 2.0% and 3.0% by volume of the anti-microbial composition of Example 1 were tested.

The microorganisms used were:

| | |
|---|---|
| Methicillin resistant *staph aureus* (MRSA) | NCTC11940/2.1 × $10^5$ CFU/ml |
| *Pseudomonas aeruginosa* | NCIMB12469/2.9 × $10^5$ CFU/ml |
| *Eschericia coli* | NCTC9001/2.2 × $10^5$ CFU/ml |

Method

The selected microorganism (0.1 ml) was transferred to each of the coated panels. A sheet of sterile plastic (5 cm×5 cm) was placed onto the microorganism, which was then carefully spread to fill the area covered by the plastic film.

The first set of samples was processed immediately on completion of the above procedure, i.e. at 0 min.

The plastic film was removed and placed onto a ceramic tile, ensuring that the surface that had been in contact with the contaminated plate was uppermost. The exposed surface was then swabbed to remove all traces of the microorganism and the swab was transferred to 10 ml of maximum recovery diluent (MRD). A second swab was used to swab the contaminated area on the surface of the panel. This swab was also transferred to the same vial of MRD and the vial was allowed to stand for 10 min to ensure that the swabs were well soaked. The vial was then whirlmixed thoroughly for 10 seconds.

The resulting mixture (0.1 ml) was then transferred onto nutrient agar plates and the plates were incubated at 37° C. for 48 hours.

The procedure was repeated on a further two sets of samples after a 30 min and 16 hour contact period at 25° C.

Results

The results of the tests undertaken on the coated panels are detailed in Table 16, 17 and 18. The results in Table 16 should be read as the base data with which the results obtained after 30 min and 16 hours are compared. However, it is clear from the variation is the results that recovery of the contaminating organisms is not entirely consistent.

TABLE 16

Time 0 min (counts per plate)

| Sample | 1.5% | 2.0% | 3.0% | Control |
|---|---|---|---|---|
| MRSA | 99 | 79 | 131 | 102 |
|  | 116 | 100 | 111 | 90 |
|  | 101 | 107 | 80 | 122 |
| E. coli | 105 | 98 | 118 | 142 |
|  | 100 | 110 | 88 | 108 |
|  | 138 | 86 | 69 | 127 |
| P. aeruginosa | 103 | 100 | 139 | 115 |
|  | 152 | 97 | 110 | 107 |
|  | 112 | 136 | 87 | 128 |

TABLE 17

Time 30 min (counts per plate)

| Sample | 1.5% | 2.0% | 3.0% | Control |
|---|---|---|---|---|
| MRSA | 9 | 1 | 0 | 79 |
|  | 16 | 0 | 0 | 66 |
|  | 2 | 0 | 0 | 84 |
| E. coli | 7 | 0 | 1 | 91 |
|  | 4 | 1 | 3 | 87 |
|  | 12 | 2 | 0 | 70 |
| P. aeruginosa | 18 | 4 | 5 | 103 |
|  | 11 | 14 | 9 | 97 |
|  | 16 | 10 | 5 | 111 |

TABLE 18

Time 16 hours (counts per plate)

| Sample | 1.5% | 2.0% | 3.0% | Control |
|---|---|---|---|---|
| MRSA | 2 | 0 | 0 | 65 |
|  | 1 | 0 | 0 | 44 |
|  | 0 | 0 | 0 | 51 |
| E. coli | 0 | 0 | 0 | 39 |
|  | 0 | 0 | 0 | 41 |
|  | 0 | 0 | 0 | 22 |
| P. aeruginosa | 0 | 0 | 0 | 79 |
|  | 0 | 0 | 0 | 59 |
|  | 0 | 0 | 0 | 61 |

Conclusion

The results in Table 17 show that, even after 30 minutes contact, the antibacterial effect of the anti-microbial composition is evident. The consistently higher counts obtained from the control panel support this. In addition, there is a significant difference between the counts from the test panel containing 1.5% by volume of the anti-microbial composition and from the test panels containing 2.0% and 3.0% by volume of the anti-microbial composition, again supporting the antibacterial effect of the composition of the invention.

The counts detailed in Table 18 after 16 hours contact also endorse the antibacterial effect of the anti-microbial composition although the consistently lower control figures suggest that there may have been a drying out effect during incubation.

The results demonstrate that the anti-microbial composition of the invention confers an antibacterial effect on the panel coatings, giving the most effective kill at an inclusion rate 2.0% by volume or greater.

The invention claimed is:

1. An anti-microbial composition consisting essentially of:
   (i) at least one anti-microbial agent, wherein at least one of the anti-microbial agents is an anti-microbial agent having a high surface tension of from 20 to 35 mN/m, and is selected from the group consisting of (a) a quarternary ammonium compound having the general formula $R^1R^2R^3R^4N^+X^-$, in which one or two of the R groups are alkyl substituted by aryl or interrupted by aryl or oxygen and the other R groups are the same or different and are $C_1$ to $C_4$ alkyl groups, (b) a dialkyldimethylammonium compound wherein the two non-methyl alkyl groups are selected from alkyl groups comprising from 8 to 12 carbon atoms, and (c) a benzalknoium halide or an aryl ring substituted benzalkonium halide,
   (ii) a compound having a low surface tension of from 8 to 14 mN/m, and selected from the group consisting of silanes, soya lecithins, polydimethylsiloxanes, and polydimethylhydroxysiloxanes, and
   (iii) at least one polar solvent, wherein in use the anti-microbial composition acts substantially to reduce or control the formation of microbial colonies on or at a surface to which the composition is applied.

2. An anti-microbial composition according to claim 1, wherein the low surface tension of the compound (ii) is 10 mN/m.

3. An anti-microbial composition according to claim 1, wherein at least one of the anti-microbial agents is of a polar nature.

4. An anti-microbial composition according to claim 1, comprising the at least one anti-microbial agent selected from bacteriocidal, fungicidal, algicidal, yeasticidal and moldicidal agents.

5. An anti-microbial composition according to claim 1, wherein the at least one anti-microbial agents is selected from benzenemethanaminium N-dodecyl-N,N-dimethylchloride, and benzyl-$C_{12}$-$C_{16}$-alkyldimethyl-ammoniumchloride.

6. An anti-microbial composition according to claim 1, wherein the at least one anti-microbial agents is selected from an amphoteric compound, an iodophore, a phenolic compound, a quaternary ammonium compound, a hypochlorite and a nitrogen based heterocyclic compound.

7. An anti-microbial composition according to claim 6, wherein the phenolic compound is selected from a methyl, ethyl, butyl, halo and aryl substituted phenol.

8. An anti-microbial composition according to claim 6, wherein the compound is selected from 2-phenylphenol, 2-benzyl-4-chlorophenol, 2-cyclopentanol-4-chlorophenol, 4-t-amylphenol, 4-t-butylphenol, 4-chloro-2-pentylphenol, 6-chloro-2-pentylphenol, p-chlorometa-xylenol, 2,4,4-trichloro-2-hydroxydiphenol, thymol, 2-i-propyl-3-methylphenol, chlorothymol, 3-methyl-4-chlorophenol, 2,6-dichloro-4-n-alkyl phenols, 2,4-dichloro-meta-xylenol, 2,4,6-trichlorophenol and 2-benzyl-4-chlorophenol.

9. A composition according to claim 1, wherein the at least one anti-microbial agents is selected from benzenemethanaminium N-dodecyl-N,N-dimethylchloride, and benzyl-$C_{12}$-$C_{16}$-alkyldimethyl-ammoniumchloride, and at least one additional anti-microbial agent is selected from 2-phenylphenol, 2-octyl-2H-isothiazol-3-one, 5-chloro-2-methyl-2H-isothiazol-3-one and 2-methyl-2H-isothiazol-3-one.

10. An anti-microbial composition according to claim 1, comprising from 1 to 4% by volume of the compound (ii).

11. An anti-microbial composition according to claim 1, wherein the at least one polar solvent is selected from water, an alcohol, an ester, a hydroxyl or glycol ester, a polyol, a ketone, and mixtures thereof.

12. An anti-microbial composition according to claim 1, wherein the at least one polar solvent is selected from n-propanol, water, isopropanol, diethylene glycol and dipropylene glycol.

13. An anti-microbial composition according to claim 1, comprising from 1 to 70% by volume of the at least one polar solvent.

14. A formulation comprising the anti-microbial composition according to claim 1, and a functional material.

15. A formulation according to claim 14, wherein the functional material is selected from plastics, fibres, coatings, films, laminates, adhesives, sealants, clays, china, ceramics, concrete, sand, paints, varnishes, lacquers, cleaning agents and settable or curable compositions such as fillers, grouts, mastics and putties.

16. A formulation according to claim 14, wherein the formulation comprises from 0.1 to 5.0% by weight of the anti-microbial composition.

17. A formulation according to claim 14, wherein the formulation comprises from 0.5 to 2.0% by weight of the anti-microbial composition.

18. A method of reducing or controlling the formulation of colonies of microorganisms on a surface, which method comprises applying the anti-microbial composition according to claim 1 to the surface.

19. A method of reducing or controlling the formulation of colonies of microorganisms on the surface, which method comprises applying the formulation of claim 14 to the surface.

20. A method of reducing or controlling the formulation of colonies of microorganisms on the surface, which method comprises applying the formulation of claim 15 to the surface.

21. A method of reducing or controlling the formulation of colonies of microorganisms on the surface, which method comprises applying the formulation of claim 16 to the surface.

22. A method of reducing or controlling the formulation of colonies of microorganisms on the surface, which method comprises applying the formulation of claim 17 to the surface.

23. A method of manufacturing the anti-microbial composition according to claim 1, the method comprising the steps of (a) mixing the anti-microbial agents together, (b) adding the compound (ii) to the anti-microbial agent(s), (c) adding the at least one polar solvent to the mixture of the at least one compound (ii) and anti-microbial agent(s) and (d) agitating the resulting mixture until a clear solution is formed.

24. A method of manufacturing a formulation comprising the step of adding the anti-microbial composition of claim 1 to a functional material.

25. An anti-microbial composition according to claim 1, wherein the compound (ii) is selected from polydimethylsiloxanes and polydimethylhydrosiloxanes.

26. An anti-microbial composition containing as a solvent a polar solvent which is selected from the group consisting of water, at least one alcohol, at least one glycol ester, at least one polyol, at least one ketone or a mixture thereof, and comprising:
  (i) at least one anti-microbial agent, wherein at least one of the anti-microbial agents is an anti-microbial agent having a high surface tension of from 20 to 35 mN/m and selected from the group consisting of (a) a quaternary ammonium compound having the general formula $R^1R^2R^3R^4N^+X^-$, in which one or two of the R groups are alkyl substituted by aryl or interrupted by aryl or oxygen and the other R groups are the same or different and are $C_1$ to $C_4$ alkyl groups, (b) a dialkyldimethylammonium compound wherein the two non-methyl alkyl groups are selected from medium and long chain alkyl groups comprising from 8 to 12 carbon atoms, and (c) a benzalkonium halide or an aryl ring substituted benzalkonium halide; and
  (ii) a compound having a low surface tension of from 8 to 14 mN/m and selected from the group consisting of silanes, soya lecithins, polydimethylsiloxanes, and polydimethylhydroxysiloxanes, wherein in use the anti-microbial composition acts substantially to reduce or control the formation of microbial colonies on or at a surface to which the composition is applied.

27. An anti-microbial composition according to claim 26, wherein the low surface tension of the compound (ii) is 10 mN/m.

28. An anti-microbial composition according to claim 26 comprising at least one additional anti-microbial agent.

29. An anti-microbial composition according to claim 28, wherein the at least one anti-microbial agents is of a polar nature.

30. An anti-microbial composition according to claim 26 comprising the at least one anti-microbial agent selected from bacteriocidal, fungicidal, algicidal, yeasticidal and moldicidal agents.

31. An anti-microbial composition according to claim 26, wherein the at least one anti-microbial agents is selected from benzenemethanaminium N-dodecyl-N,N-dimethylchloride, and benzyl-$C_{12}$-$C_{16}$-alkyldimethyl-ammoniumchloride.

32. An anti-microbial composition according to claim 28, wherein the at least one additional anti-microbial agent is selected from amphoteric compounds, iodophores, phenolic compounds, quarternary ammonium compounds, hypochlorites and nitrogen-based heterocyclic compounds.

33. An anti-microbial composition according to claim 32, wherein the phenolic compound is selected from a methyl, ethyl, butyl, halo and aryl substituted phenol.

34. An anti-microbial composition according to claim 32, wherein the phenolic compound is selected from 2-phenylphenol, 2-benzyl-4-chlorophenol, 2-cyclopentanol-4-chlorophenol, 4-t-amylphenol, 4-t-butylphenol, 4-chloro-2-pentylphenol, 6-chloro-2-pentylphenol, p-chlorometa-xylenol, 2,4,4-trichloro-2-hydroxydiphenol, thymol, 2-i-propyl-3-methylphenol, chlorothymol, 3-methyl-4-chlorophenol, 2,6-dichloro-4-n-alkyl phenols, 2,4-dichloro-meta-xylenol, 2,4,6-trichlorophenol and 2-benzyl-4-chlorophenol.

35. A composition according to claim 28, wherein the at least one anti-microbial agents is selected from benzenemethanaminium N-dodecyl-N,N-dimethylchloride and benzyl-$C_{12}$-$C_{16}$-alkyldimethyl-ammoniumchloride, and at least one of the additional anti-microbial agents is selected from 2-phenylphenol, 2-octyl-2H-isothiazol-3-one, 5-chloro-2-methyl-2H-isothiazol-3-one, and 2-methyl-2H-isothiazol-3-one.

36. An anti-microbial composition according to claim 26, comprising from 1 to 4% by volume of the compound (ii).

37. An anti-microbial composition according to claim 26, wherein the polar solvent is selected from n-propanol, water, isopropanol, diethylene glycol, dipropylene glycol and mixtures thereof.

38. An anti-microbial composition according to claim 26, comprising from 1 to 70% by volume of the polar solvent.

39. An anti-microbial composition according to claim 26, wherein the compound (ii) is selected from polydimethylsiloxanes and polydimethylhydrosiloxanes.

40. A formulation comprising the anti-microbial composition according to claim 26, and a functional material.

41. A formulation according to claim 40, wherein the functional material is selected from plastics, fibres, coatings, films, laminates, adhesives, sealants, clays, china, ceramics, concrete, sand, paints, varnishes, lacquers, cleaning agents and settable or curable compositions such as fillers, grouts, mastics and putties.

42. A formulation according to claim 40, wherein the formulation comprises from 0.1 to 5.0% by weight of the anti-microbial composition.

43. A formulation according to claim 40, wherein the formulation comprises from 0.5 to 2.0% by weight of the anti-microbial composition.

44. A method of reducing or controlling the formulation of colonies of microorganisms on the surface, which method comprises applying the anti-microbial composition according to claim 26 to the surface.

45. A method of reducing or controlling the formulation of colonies of microorganisms on the surface, which method comprises applying the formulation of claim 40 to the surface.

46. A method of reducing or controlling the formulation of colonies of microorganisms on the surface, which method comprises applying the formulation of claim 41 to the surface.

47. A method of reducing or controlling the formulation of colonies of microorganisms on the surface, which method comprises applying the formulation of claim 42 to the surface.

48. A method of reducing or controlling the formulation of colonies of microorganisms on the surface, which method comprises applying the formulation of claim 43 to the surface.

49. A method of manufacturing the anti-microbial composition according to claim 26, the method comprising the steps of (a) mixing the anti-microbial agents together, (b) adding the compound (ii) to the mixture of step (a), (c) adding the polar solvent to the mixture of step (b), and (d) agitating the resulting mixture until a clear solution is formed.

50. A method of manufacturing a formulation comprising the step of adding the anti-microbial composition of claim 26 to a functional material.

51. An antimicrobial composition according to claim 25, wherein the compound (ii) is selected from the group consisting of polydimethylsiloxane having a chain length of from $C_{12}$ to $C_{20}$ and polydimethylhydrosiloxane having a chain length of from $C_{12}$ to $C_{20}$.

52. An antimicrobial composition according to claim 39, wherein the compound (ii) is selected from the group consisting of polydimethylsiloxane having a chain length of from $C_{12}$ to $C_{20}$ and polydimethylhydrosiloxane having a chain length of from $C_{12}$ to $C_{20}$.

53. An anti-microbial composition consisting essentially of:
  (i) at least two anti-microbial agents, wherein at least one of the anti-microbial agents is an anti-microbial agent having a high surface tension of from 20 to 35 mN/m, and is selected from the group consisting of (a) a quarternary ammonium compound having the general formula $R^1R^2R^3R^4N^+X^-$, in which one or two of the R groups are alkyl substituted by aryl or interrupted by aryl or oxygen and the other R groups are the same or different and are $C_1$ to $C_4$ alkyl groups, (b) a dialkyldimethylammonium compound wherein the two non-methyl alkyl groups are selected from alkyl groups comprising from 8 to 12 carbon atoms, and (c) a benzalknoium halide or an aryl ring substituted benzalkonium halide,
  (ii) a compound having a low surface tension of from 8 to 14 mN/m, and selected from the group consisting of silanes, soya lecithins, polydimethylsiloxanes, and polydimethylhydroxysiloxanes, and
  (iii) a polar solvent, wherein in use the anti-microbial composition acts substantially to reduce or control the formation of microbial colonies on or at a surface to which the composition is applied.

* * * * *

UNITED STATES PATENT AND TRADEMARK OFFICE
CERTIFICATE OF CORRECTION

| | | |
|---|---|---|
| PATENT NO. | : 7,674,473 B2 | Page 1 of 1 |
| APPLICATION NO. | : 10/039677 | |
| DATED | : March 9, 2010 | |
| INVENTOR(S) | : Stephen Brian Falder and David Rawden | |

It is certified that error appears in the above-identified patent and that said Letters Patent is hereby corrected as shown below:

Column 6, lines 61-62 replace the term "methylbenzalkomium" with the term
-- methylbenzalkonium --.
Column 16, line 31 insert a -- . -- between the terms "half and "The".
Column 20, line 7 replace the term "30° C." with the term -- 30°C --.
In Column 22:
Line 32 replace the term "10° C." with the term -- 10°C --.
Line 34 insert a -- - -- between the terms "anti" and "microbial".
Column 22, line 64 replace the terms "10° C. (+/-1° C.)" with the terms -- 10°C (+/- 1°C) --.
Column 23, line 8 replace the terms "37° C. (+/-1° C.)" with the terms -- 37°C (+/- 1°C) --.
Column 24, line 18 replace the term "10° C.," with the term -- 10°C, --.
Column 26, line 54 replace the term " whirlmixed" with the term -- whirlimixed --.

Signed and Sealed this
Twelfth Day of April, 2011

David J. Kappos
*Director of the United States Patent and Trademark Office*